(12) United States Patent
Stewart, Jr. et al.

(10) Patent No.: US 12,142,369 B2
(45) Date of Patent: Nov. 12, 2024

(54) ENTERPRISE COMPUTER SYSTEM FOR MEDICAL DATA PROCESSING

(71) Applicant: JTS Ventures, Inc., Norcross, GA (US)

(72) Inventors: Thomas David Stewart, Jr., Norcross, GA (US); Julie Antoniette Echols Stewart, Norcross, GA (US); Chris Merle Langley, Newport, RI (US); Randal Lawrence Wynn, Land O Lakes, FL (US)

(73) Assignee: JTS Ventures, Inc., Norcross, GA (US)

( * ) Notice: Subject to any disclaimer, the term of this patent is extended or adjusted under 35 U.S.C. 154(b) by 0 days.

(21) Appl. No.: 18/117,909

(22) Filed: Mar. 6, 2023

(65) Prior Publication Data

US 2023/0386650 A1    Nov. 30, 2023

Related U.S. Application Data

(63) Continuation of application No. 17/379,219, filed on Jul. 19, 2021.
(Continued)

(51) Int. Cl.
*G16H 40/20* (2018.01)
*G06Q 10/0637* (2023.01)
(Continued)

(52) U.S. Cl.
CPC ....... *G16H 40/20* (2018.01); *G06Q 10/06375* (2013.01); *G06Q 40/08* (2013.01);
(Continued)

(58) Field of Classification Search
CPC ........ G16H 40/20; G16H 10/60; G16H 70/20; G16H 70/60; G06Q 10/06375; G06Q 40/08; G06Q 40/12; G06Q 50/26
See application file for complete search history.

(56) References Cited

U.S. PATENT DOCUMENTS

| 2011/0258004 | A1* | 10/2011 | Dean | G06Q 10/10 |
| | | | | 705/4 |
| 2016/0019357 | A1* | 1/2016 | Marzula | G06Q 10/10 |
| | | | | 705/2 |

(Continued)

FOREIGN PATENT DOCUMENTS

CN          109767067 A   *  5/2019

*Primary Examiner* — A. Hunter Wilder
(74) *Attorney, Agent, or Firm* — Locke Lord LLP; Christopher J. Capelli

(57) ABSTRACT

A computer system and method for generating non-fungible tokens (NFTs) representing a company asset based on evaluation of company assets (e.g., a hospital). Stored in a database are one or more digital assets (e.g., one or more of settlement rights and insurance claim payment obligations) representative of contractual obligations owed to the company (e.g., settlement rights), which are then analyze to determine one or more assets owed to the company. A valuation value is then determined for the determined one or more assets. NFTs are then generated based on the determined valuation value of the determined one or more assets. Additionally, the generated NFTs may be leveraged as collateral in an underwriting process. Further, analyzed in real-time, is a revenue cycle management of the company for generating a risk-weighted index value indicative of the revenue cycle management.

12 Claims, 30 Drawing Sheets

Related U.S. Application Data

(60) Provisional application No. 63/053,432, filed on Jul. 17, 2020.

(51) Int. Cl.
*G06Q 40/08* (2012.01)
*G06Q 40/12* (2023.01)
*G06Q 50/26* (2024.01)
*G16H 10/60* (2018.01)
*G16H 70/20* (2018.01)
*G16H 70/60* (2018.01)

(52) U.S. Cl.
CPC ............. *G06Q 40/12* (2013.12); *G16H 10/60* (2018.01); *G16H 70/20* (2018.01); *G16H 70/60* (2018.01); *G06Q 50/26* (2013.01)

(56) References Cited

U.S. PATENT DOCUMENTS

2020/0342539 A1\* 10/2020 Doney ............... G06Q 20/3829
2021/0295324 A1\* 9/2021 Kerseboom ............ H04L 9/3239
2023/0116401 A1\* 4/2023 Nichani ............... G06Q 20/123
705/36 R \* cited by examiner ACME / JTShealth partners — DEMO Cash Report

Daily Cash Collections

| Post Date | A. Net Payments | B. Payment | Takeback |
|---|---:|---:|---:|
| 12/02/2019 | $826,096 | $826,096.32 | $0.00 |
| 12/03/2019 | $85,771 | $85,770.95 | $0.00 |
| 12/04/2019 | $3,084,124 | $3,084,123.96 | $0.00 |
| 12/05/2019 | $206,411 | $206,410.95 | $0.00 |
| 12/11/2019 | ($15,221) | $0.00 | $15,221.32 |
| 12/12/2019 | $238,281 | $238,281.40 | $0.00 |
| 12/26/2019 | $797 | $796.51 | $0.00 |
| Total | $4,426,259 | $4,441,480.09 | $15,221.32 |

Net Payments:

Report contains a hierarchy view where you can drill down to summarize data by payor group, plan and receivable group bill period.

Takebacks:

You can identify takebacks quickly and investigate the cause. The report again contains a hierarchy where you can easily identify the account by drilling down onto the RG level.

FIG. 5

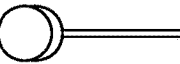
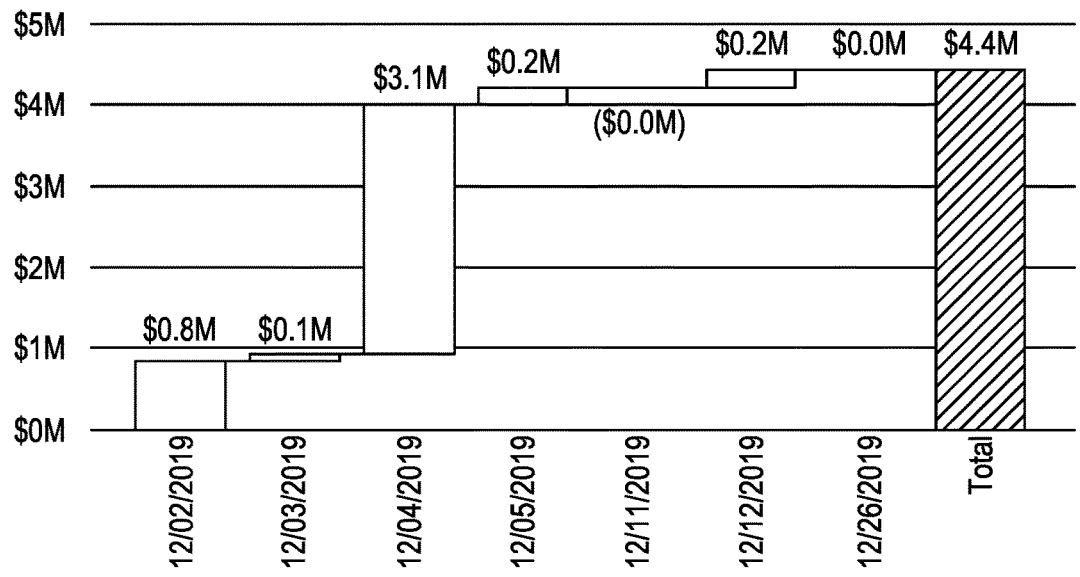
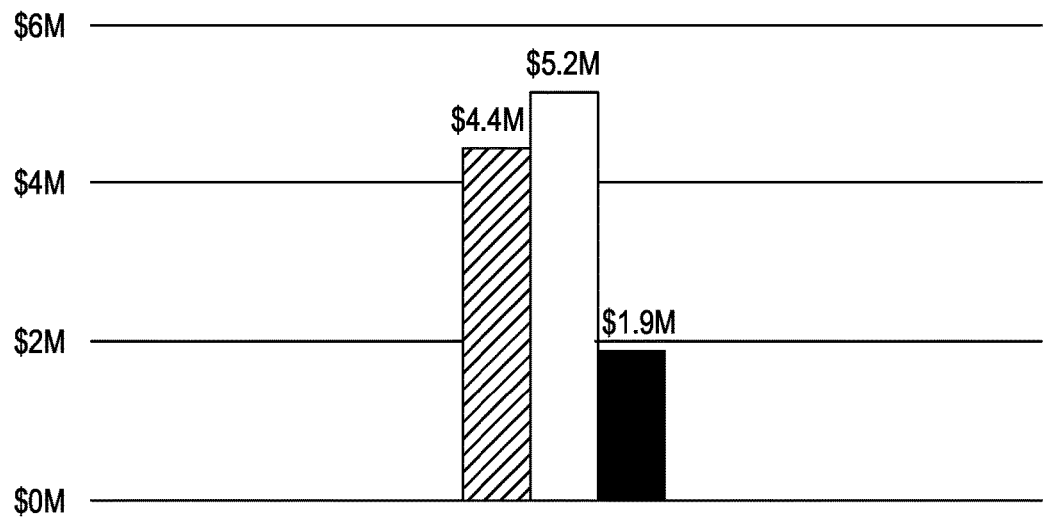
*FIG. 5 Continued*

| Payor Group | Client | Sector |
|---|---|---|
| All ⌄ | Acme Center ⌄ | All ⌄ |

Goal Attainment

| Payor Group | Net Payment MTD | Monthly Goal | Cash Remaining | % Of Goal |
|---|---|---|---|---|
| Blues | $3,910,220 | $1,506,963 | ($2,403,257) | 259.48% |
| Comm | $358,921 | $67,807 | ($291,114) | 529.33% |
| Managed Care | | $37,762 | $37,762 | |
| Medicaid | | $28,005 | $28,005 | |
| Medicaid HMO | $156,321 | $151,418 | ($4,902) | 103.24% |
| Medicare | | $9,417 | $9,417 | |
| Other | $797 | $5,130 | $4,333 | 15.53% |
| Tricare | | $51,953 | $51,953 | |
| Total | $4,426,259 | $1,858,455 | ($2,567,804) | 238.17% |

<u>Monthly Goal:</u> Looks at your AR and understands what will flow into your inventory inventory (if applicable) and project a monthly goal based on historical collections. If an account is paid before it reaches your inventory the monthly goal will understand and adjust to goal. The goal is also adjustable by percentage AR 238.17% ✓

Goal: 100% (+138.17%)

FIG. 5 Continued

Collection Rate

Cash Collections Rate

| Calendar Year | Payment | Gross Collection Rate | Adjusted Collections Rate |
|---|---|---|---|
| 2020 | $3,043,516.24 | 12.57% | 67.18% |
| Jan 2020 | $3,043,516.24 | 12.57% | 67.18% |
| Blues | $3,010,670.82 | 22.36% | 56.06% |
| Comm | $15,602.41 | 0.51% | 84.77% |
| Managed Care | | | 69.77% |
| Medicaid | | | 69.00% |
| Medicaid HMO | | | 57.55% |
| Medicare | | | 93.61% |
| Other | $1,446.52 | 0.26% | 69.06% |
| Tricare | $15,796.50 | 0.87% | 79.37% |
| Total | $3,043,516.24 | 12.57% | 67.18% |

*FIG. 6*

JTShealth partners

| Payor Group | Client | Sector |
|---|---|---|
| All ⌄ | Acme Center ⌄ | All ⌄ |

Collection Rate

| Payor Group | Payment | Gross Collection Rate | Adjusted Collections Rate |
|---|---|---|---|
| Blues | $3,010,670.82 | 22.36% | 56.06% |
| Tricare | $15,796.50 | 0.87% | 79.37% |
| Comm | $15,602.41 | 0.51% | 84.77% |
| Other | $1,446.52 | 0.26% | 69.06% |
| Managed Care | | | 69.77% |
| Medicaid | | | 69.00% |
| Medicaid HMO | | | 57.55% |
| Medicare | | | 93.61% |
| Total | $3,043,516.24 | 12.57% | 67.18% |

*FIG. 6 Continued*

Number of Days Since Last JTS Comment

| Days | 0-30 | | 31-60 | | -91+ | | Total | |
|---|---|---|---|---|---|---|---|---|
| Payor Group | Accounts | Balance | Accounts | Balance | Accounts | Balance | Accounts | Balance |
| Comm | 32 | $8,263,117.47 | 1 | $15,089.29 | 1 | $15,089.29 | 34 | $8,293,296.05 |
| Blues | 27 | $8,206,030.94 | 1 | $1,691,910.08 | 2 | $316,007.74 | 30 | $10,213,948.77 |
| Other | 11 | $319,674.08 | 3 | $69,270.46 | 3 | $180,455.06 | 17 | $569,399.59 |
| Medicaid HMO | 15 | $1,773,407.20 | | | 1 | $0.00 | 16 | $1,773,407.20 |
| Medicare | 11 | $1,174,397.57 | 1 | $0.00 | 2 | $0.00 | 14 | $1,174,397.57 |
| Managed Care | 6 | $1,582,132.79 | | | | | 6 | $1,582,132.79 |
| Workers Comp | 1 | $1,411,383.91 | 1 | $36,104.71 | | | 6 | $1,447,488.62 |
| Tricare | 4 | $2,945,324.02 | | | | | 4 | $2,945,324.02 |
| Total | 96 | $25,675,467.98 | 6 | $1,812,374.54 | 7 | $511,552.09 | 109 | $27,999,394.61 |

FIG. 7

Age Trial Balance

| Week | | Sunday, January 26, 2020 | | | | |
|---|---|---|---|---|---|---|
| Age Range A | Account Count | Balance | Account Count Chg FW% | Account Count Chg PW% | Balance Chg FW% | Balance Chg PW% |
| +365 | 32 | $14,215,440 | 146.15% | -11.11% | 124.89% | 1.35% |
| +365 | 32 | $14,215,440 | 146.15% | -11.11% | 124.89% | 1.35% |
| 121 - 365 | 26 | $1,421,795 | 225.00% | 36.84% | 60.71% | -34.80% |
| 301 - 330 | 10 | $342,661 | 400.00% | -9.09% | -47.16% | 108.87% |
| 331 - 365 | 16 | $1,079,134 | 166.67% | 100.00% | 356.91% | -46.49% |
| Total | 58 | $15,637,235 | 176.19% | 5.45% | 117.01% | -3.52% |

Note:
Acme Center's First Week data is from 2/17/2019

FW (First Week)   PW (Prior Week)

*FIG. 8*

Recovery Opportunity Analysis
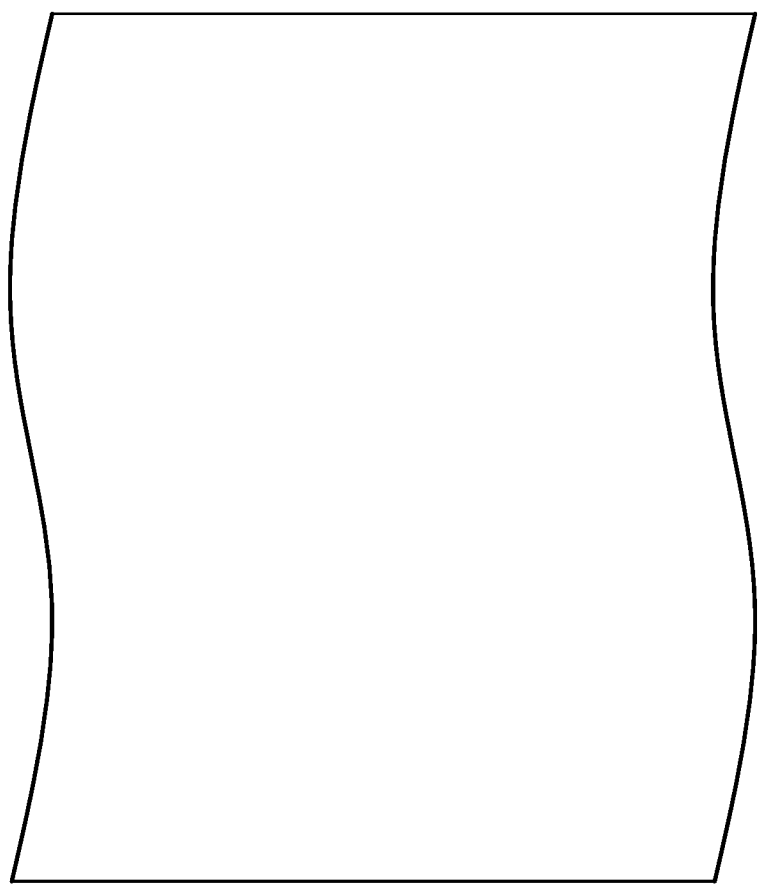
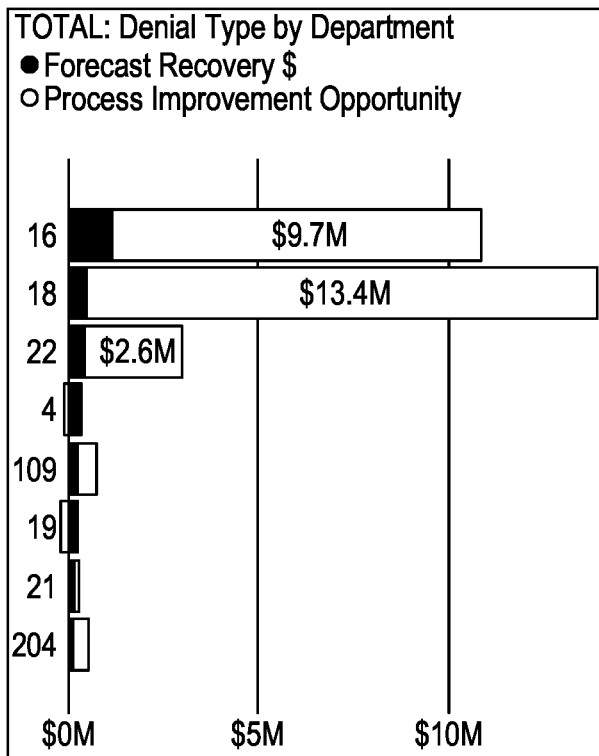
*FIG. 12 Continued*

Part 1: Financial Health Rating (RCM + Capacity) | FICO Analogy - Example

Financial Health Rating

| Metrics | Overdue | Behind | Astrisk | On track | Not Sorted | Completed |
|---|---|---|---|---|---|---|
| 6 | 0 | 0 | 1 | 5 | 0 | 0 |

| Name | Owners | Status | Value | Progress | Due date |
|---|---|---|---|---|---|
| Denial Rate | Randal Wynn | On Track | 4.7/0 | | Dec 31, 2022 |
| % or AR over 90 | Randal Wynn | At risk | 29.00%/10.00% | | Dec 31, 2022 |
| Clear Claim Rate | Randal Wynn | On track | 91.00%/100.00% | | Dec 31, 2022 |
| DNFB Days | Randal Wynn | On track | 3.2/1.0 | | Dec 31, 2022 |
| Cash Postition | Randal Wynn | On track | $1.10M/1.40M | | Dec 31, 2022 |
| Total Weighted Score | Randal Wynn | On track | 8.90/10 | | Dec 31, 2022 |

*FIG. 13*

ENTERPRISE COMPUTER SYSTEM FOR MEDICAL DATA PROCESSING

CROSS REFERENCE TO RELATED APPLICATIONS

This application is a continuation-in-part of U.S. patent application Ser. No. 17/379,219 filed Jul. 19, 2021, which claims priority to U.S. Patent Application Ser. No. 63/053,432 filed Jul. 17, 2020 which is incorporated herein by reference in its entirety.

FIELD OF THE INVENTION

The present application generally relates to systems, methods and program products for analyzing and/or improving performance for enterprise computer systems. In particular, certain illustrated embodiments provide improvements for generating score values indicative of underwriting values for generating non-fungible tokens for collateral purposes.

BACKGROUND OF THE INVENTION

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may also correspond to claimed embodiments.

Client organizations, such as hospitals and insurance companies, with datasets in their databases often benefit from predictive analysis. Currently, there is no low cost and scalable solution in the marketplace today. Instead, client organizations typically hire technical experts to develop customized mathematical constructs and predictive models, which are often costly and require large amounts of time. Consequently, client organizations without vast financial means often do not have access to predictive analysis capabilities for their datasets.

Client organizations that have the financial means to hire technical and mathematical experts to develop the necessary mathematical constructs and predictive models suffer from a common problem with customized solutions. Specifically, the customized solution is tailored to the particular problem at hand at a given point in time, and as such, the customized solution is not able to accommodate changes to the underlying data structure, the customized solution is not able to accommodate changes to the types of data stored within the client's datasets, nor is the customized solution able to scale up to meet increasing and changing demands of the client as their business and dataset grows over time.

For instance, with specific regards to audits, they were typically performed manually which limited the extent and exactness of a complete audit. Further it is desirable to provide the ability to compare large amounts of data at both a high-level comparison view, and easily provide a breakdown and analyzed data (e.g., with very few mouse clicks) to the account level detail, which is not currently available from existing reporting tools.

The present state of the art may therefore benefit from systems and methods for predictive query implementation and usage in an on-demand and/or multi-tenant database system as described herein.

SUMMARY OF THE INVENTION

The purpose and advantages of the below described illustrated embodiments will be set forth in and apparent from the description that follows. Additional advantages of the illustrated embodiments will be realized and attained by the devices, systems and methods particularly pointed out in the written description and claims hereof, as well as from the appended drawings.

To achieve these and other advantages and in accordance with the purpose of the illustrated embodiments, in one aspect, the illustrated embodiments relate to a computer system and method for generating non-fungible tokens (NFTs) representing a company asset based on evaluation of company assets (e.g., a hospital). Stored in a database are one or more digital assets (e.g., one or more of settlement rights and insurance claim payment obligations) representative of contractual obligations owed to the company (e.g., settlement rights), which are then analyze to determine one or more assets owed to the company. A valuation value is then determined for the determined one or more assets. NFTs are then generated based on the determined valuation value of the determined one or more assets. Additionally, the generated NFTs may be leveraged as collateral in an underwriting process. Further, analyzed in real-time, is a revenue cycle management of the company for generating a risk-weighted index value indicative of the revenue cycle management.

Additional embodiments relate to a computer system and method for performing analytics on electronic data containing information regarding inpatient population to identify one or more inpatient records that were coded and/or reimbursed incorrectly so as to generate an electronic report indicating a return-on-investment (ROI) scenario when coding is corrected. Utilized are one or more of MS-DRG codes and code sets, payer, length of stay, and ICD codes to determine a preliminary list of inpatient records coded and reimbursed incorrectly. A visual user-based report is generated that indicates a return-on-investment scenario if the electronic data containing information regarding inpatient population is corrected and rebilled based on user prescribed criteria.

Other embodiments generally relate to data analytics, data integration, processing, and more particularly relates to a machine learning platform for analyzing and/or enhancing performance for enterprise computer systems. Provided are systematic improvements to rules and workflows employed in enterprise computer systems for enterprise analysis. An enterprise analysis system may begin an enterprise analysis process by associating, using one or more computers, a plurality of component data comprising component information of an enterprise system with respective category data comprising category information of a cognitive analysis framework, the category information including for instance (but not to be understood to be limited thereto): (a) a user activity category information associated with user interactions in the enterprise system; (b) a communication category information associated with communications produced by the enterprise system; (c) an action category information associated with actions taken by the enterprise system; (d) a knowledge category information associated with data stored by the enterprise system; and (e) a learning category information associated with feedback analytics of the enterprise system. It is to be appreciated that in certain embodiments, not all of the above categories may be used and/or other categories may be added.

It is to be understood the enterprise analysis system may store, by the one or more computers, the associated respective category data for each of the plurality of component data. The enterprise analysis system may assign, using the one or more computers, a respective weight value for each of the plurality of component data. The enterprise analysis system may store, by the one or more computers, one or more ontology's including workflow definitions, business rule definitions and/or operational data definitions.

The enterprise analysis system may analyze, using the one or more computers, the runtime behavioral data, the point-in-time operational data, the resultant operational data, and respective weight values to determine one or more first data patterns associated with an event. The enterprise analysis system may determine, using the one or more computers, one or more modified behavioral data records calculated to modify a recurrence of the event. The enterprise analysis system may generate, by the one or more computers, an electronic report identifying the one or more modified behavioral data records. The electronic report may comprise one or more inputs into a feedback process, calculated to improve performance of the process.

In particular, and in accordance with certain illustrated embodiments, provided is a first software tool providing an auditing functionality ("nCREAS" (Coding and Revenue Enhancement Analytics and Services) "HIM" (Health Information Management) Auditing Suite) operational and configured to examine one or more electronic files containing a specific set of data regarding an inpatient hospital population. Preferably utilizing "MS-DRG" (Medicare Severity-Diagnosis Related Group) codes and code sets, payer, length of stay, and "ICD" (International Classification of Diseases) codes, the tool identifies a preliminary list of inpatient records that were potentially coded and reimbursed incorrectly. Finally, a visual based report conveys return on investment ("ROI") if record is corrected and rebilled based on recommendations in addition to projecting future ROI if coding training is conducted to correct documented mistake.

And further in accordance with certain illustrated embodiments, provided is a software tool (nCREAS Analytics) configured and operational to analysis accounts receivables data, cash collections data, staff and account productivity data, revenue charge capture data, and denials data to preferably identify trends and high-value opportunities as well as process improvement opportunities. It is to be appreciated and understood that the aforementioned suite of tools may be utilized to identify trends and drill down to specific account data elements. Analytics compare client facilities & departments' performance by payer, "RG" (Receivable Group), and denial code.

It is to be appreciated and understood that in accordance with certain illustrated embodiments, the tools disclosed herein may be utilized with health care data, as well insurance data, in addition to other applicable enterprise data.

BRIEF DESCRIPTION OF THE DRAWINGS

The accompanying appendices and/or drawings illustrate various non-limiting, example, inventive aspects in accordance with the present disclosure:

FIGS. 5-12 depict various exemplary electronic reports preferably generated on a user GUI in accordance with the preferred embodiments;

FIG. 13 illustrates a generated screen shot depicting analyzed account receivables in association with determined scoring values;

DETAILED DESCRIPTION OF CERTAIN EMBODIMENTS

Figure 1:
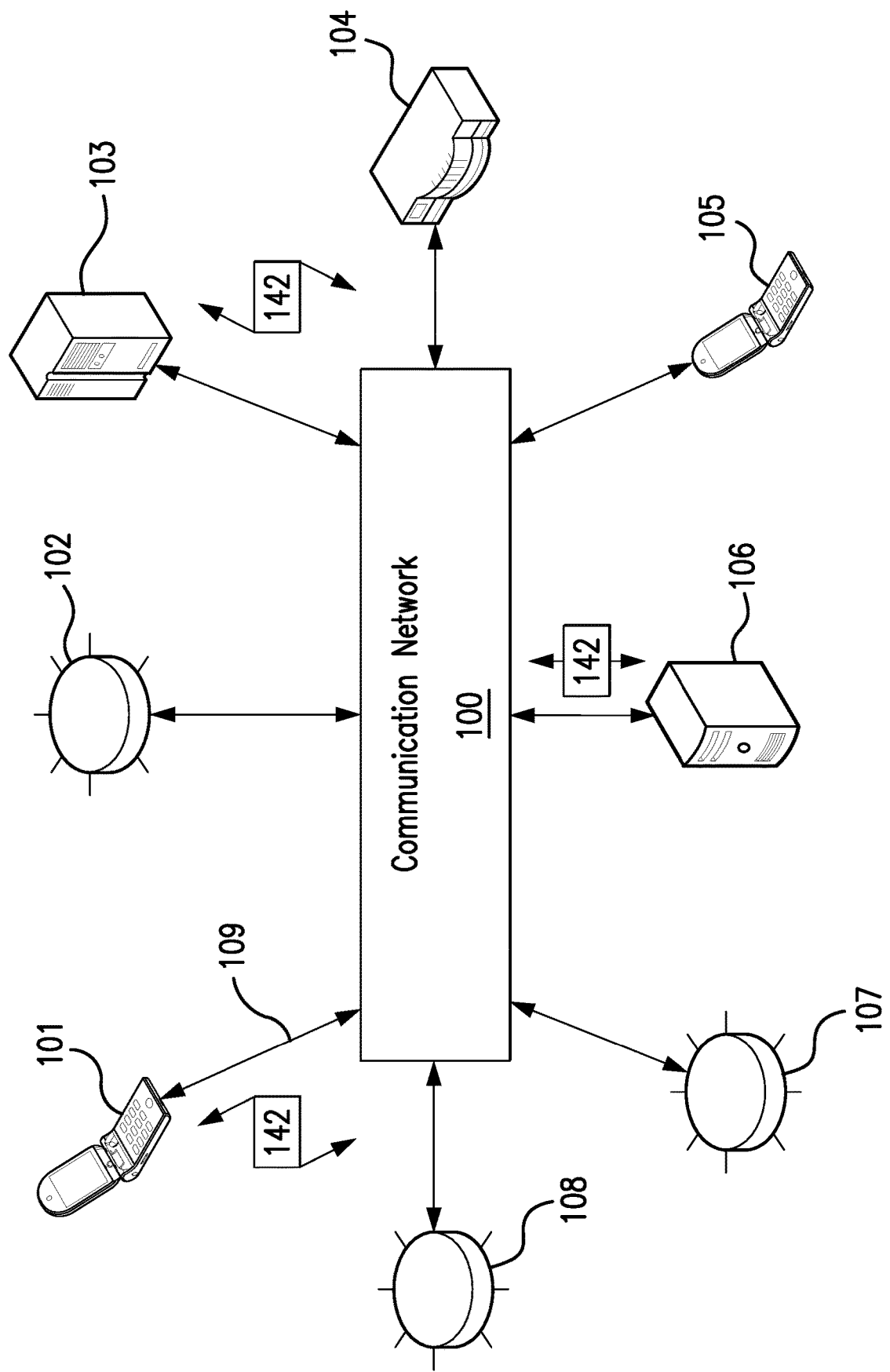
FIG. 1 illustrates an example communication network utilized with one or more illustrated embodiments.

The illustrated embodiments are now described more fully with reference to the accompanying drawings wherein like reference numerals identify similar structural/functional features. The illustrated embodiments are not limited in any way to what is illustrated as the illustrated embodiments described below are merely exemplary, which can be embodied in various forms, as appreciated by one skilled in the art. Therefore, it is to be understood that any structural and functional details disclosed herein are not to be interpreted as limiting, but merely as a basis for the claims and as a representation for teaching one skilled in the art to variously employ the discussed embodiments. Furthermore, the terms and phrases used herein are not intended to be limiting but rather to provide an understandable description of the illustrated embodiments.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the illustrated embodiments, exemplary methods and materials are now described.

It must be noted that as used herein and in the appended claims, the singular forms "a", "an," and "the" include plural referents unless the context clearly dictates otherwise. Thus, for example, reference to "a stimulus" includes a plurality of such stimuli and reference to "the signal" includes reference to one or more signals and equivalents thereof known to those skilled in the art, and so forth.

It is to be appreciated the illustrated embodiments discussed below are preferably a software algorithm, program or code residing on computer useable medium having control logic for enabling execution on a machine having a computer processor. The machine typically includes memory storage configured to provide output from execution of the computer algorithm or program.

As used herein, the term "software" is meant to be synonymous with any code or program that can be in a processor of a host computer, regardless of whether the implementation is in hardware, firmware or as a software computer product available on a disc, a memory storage device, or for download from a remote machine. The embodiments described herein include such software to implement the equations, relationships and algorithms described above. One skilled in the art will appreciate further features and advantages of the illustrated embodiments based on the above-described embodiments. Accordingly, the illustrated embodiments are not to be limited by what has been particularly shown and described, except as indicated by the appended claims.

Turning now descriptively to the drawings, in which similar reference characters denote similar elements throughout the several views, FIG. 1 depicts an exemplary communications network 100 in which below illustrated embodiments may be implemented.

It is to be understood a communication network 100 is a geographically distributed collection of nodes interconnected by communication links and segments for transporting data between end nodes, such as personal computers, work stations, smart phone devices, tablets, televisions, sensors and or other devices such as automobiles, etc. Many types of networks are available, with the types ranging from local area networks (LANs) to wide area networks (WANs). LANs typically connect the nodes over dedicated private communications links located in the same general physical location, such as a building or campus. WANs, on the other hand, typically connect geographically dispersed nodes over long-distance communications links, such as common carrier telephone lines, optical lightpaths, synchronous optical networks (SONET), synchronous digital hierarchy (SDH) links, or Powerline Communications (PLC), and others.

FIG. 1 is a schematic block diagram of an example communication network 100 illustratively comprising nodes/devices 101-108 (e.g., sensors 102, client computing devices 103, smart phone devices 105, web servers 106, routers 107, switches 108, and the like) interconnected by various methods of communication. For instance, the links 109 may be wired links or may comprise a wireless communication medium, where certain nodes are in communication with other nodes, e.g., based on distance, signal strength, current operational status, location, etc. Moreover, each of the devices can communicate data packets (or frames) 142 with other devices using predefined network communication protocols as will be appreciated by those skilled in the art, such as various wired protocols and wireless protocols etc., where appropriate. In this context, a protocol consists of a set of rules defining how the nodes interact with each other. Those skilled in the art will understand that any number of nodes, devices, links, etc. may be used in the computer network, and that the view shown herein is for simplicity. Also, while the embodiments are shown herein with reference to a general network cloud, the description herein is not so limited, and may be applied to networks that are hardwired.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object-oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Figure 2:
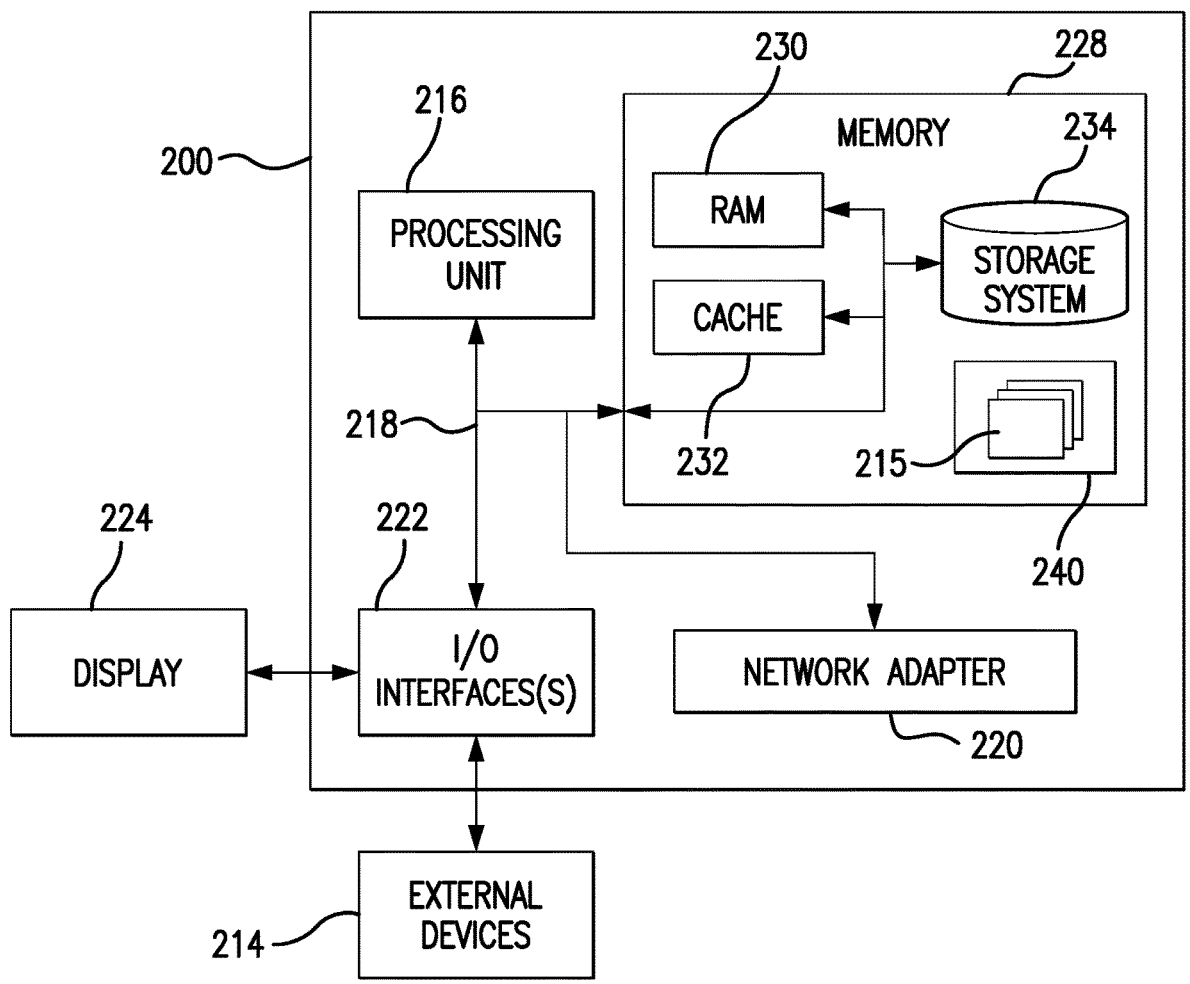
FIG. 2 illustrates an example network computer device configured to implement one or more of the illustrated embodiments.

FIG. 2 is a schematic block diagram of an example network computing device 200 (e.g., client computing device 103, server 106, etc.) that may be used (or components thereof) with one or more embodiments described herein, e.g., as one of the nodes shown in the network 100. As explained above, in different embodiments these various devices are configured to communicate with each other in any suitable way, such as, for example, via communication network 100.

Device 200 is intended to represent any type of computer system capable of carrying out the teachings of various embodiments of the present invention. Device 200 is only one example of a suitable system and is not intended to suggest any limitation as to the scope of use or functionality of embodiments of the invention described herein. Regardless, computing device 200 is capable of being implemented and/or performing any of the functionality set forth herein.

Computing device 200 is operational with numerous other general purpose or special purpose computing system environments or configurations. Examples of well-known computing systems, environments, and/or configurations that may be suitable for use with computing device 200 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, and distributed data processing environments that include any of the above systems or devices, and the like.

Computing device 200 may be described in the general context of computer system-executable instructions, such as program modules, being executed by a computer system. Generally, program modules may include routines, programs, objects, components, logic, data structures, and so on that perform particular tasks or implement particular abstract data types. Computing device 200 may be practiced in distributed data processing environments where tasks are performed by remote processing devices that are linked through a communications network. In a distributed data processing environment, program modules may be located in both local and remote computer system storage media including memory storage devices.

Device 200 is shown in FIG. 2 in the form of a specific computing device. The components of device 200 may include, but are not limited to, one or more processors or processing units 216, a system memory 228, and a bus 218 that couples various system components including system memory 228 to processor 216.

Bus 218 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computing device 200 typically includes a variety of computer system readable media. Such media may be any available media that is accessible by device 200, and it includes both volatile and non-volatile media, removable and non-removable media.

System memory 228 can include computer system readable media in the form of volatile memory, such as random access memory (RAM) 230 and/or cache memory 232. Computing device 200 may further include other removable/non-removable, volatile/non-volatile computer system storage media. By way of example only, storage system 234 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 218 by one or more data media interfaces. As will be further depicted and described below, memory 228 may include at least one program product having a set (e.g., at least one) of program modules that are configured to carry out the functions of embodiments of the invention.

Program/utility 240, having a set (at least one) of program modules 215, such as underwriting module, may be stored in memory 228 by way of example, and not limitation, as well as an operating system, one or more application programs, other program modules, and program data. Each of the operating system, one or more application programs, other program modules, and program data or some combination thereof, may include an implementation of a networking environment. Program modules 215 generally carry out the functions and/or methodologies of embodiments of the invention as described herein.

Device 200 may also communicate with one or more external devices 214 such as a keyboard, a pointing device, a display 224, etc.; one or more devices that enable a user to interact with computing device 200; and/or any devices (e.g., network card, modem, etc.) that enable computing device 200 to communicate with one or more other computing devices. Such communication can occur via Input/Output (I/O) interfaces 222. Still yet, device 200 can communicate with one or more networks such as a local area network (LAN), a general wide area network (WAN), and/or a public network (e.g., the Internet) via network adapter 220. As depicted, network adapter 220 communicates with the other components of computing device 200 via bus 218. It should be understood that although not shown, other hardware and/or software components could be used in conjunction with device 200. Examples, include, but are not limited to: microcode, device drivers, redundant processing units, external disk drive arrays, RAID systems, tape drives, and data archival storage systems, etc.

FIGS. 1 and 2 are intended to provide a brief, general description of an illustrative and/or suitable exemplary environment in which embodiments of the below described present invention may be implemented. FIGS. 1 and 2 are exemplary of a suitable environment and are not intended to suggest any limitation as to the structure, scope of use, or functionality of an embodiment of the present invention. A particular environment should not be interpreted as having any dependency or requirement relating to any one or combination of components illustrated in an exemplary operating environment. For example, in certain instances, one or more elements of an environment may be deemed not necessary and omitted. In other instances, one or more other elements may be deemed necessary and added.

With the exemplary communication network 100 (FIG. 1) and computing device 200 (FIG. 2) being generally shown and discussed above, description of certain illustrated embodiments of the present invention will now be provided. With continuing reference now to FIGS. 1 and 2, it is to be understood computing device 200 is configured and operational to provide is a software tool providing an auditing functionality (nCREAS HIM Auditing Suite) operational and configured to examine one or more electronic files containing a specific set of data regarding an inpatient hospital population. Preferably utilizing MS-DRG codes and code sets, payer, length of stay, and ICD codes, the tool identifies a preliminary list of inpatient records that were potentially coded and reimbursed incorrectly. Generated is preferably a visual based report that conveys return on investment ("ROI") if record is corrected and rebilled based on recommendations in addition to projecting future ROI if coding training is conducted to correct documented mistake.

It is to be understood that in accordance with teachings herein, device 200 may be configured and operational to collect inpatient facility data, from external (via a computer network) or internal sources, which may include one or more of MS-DRG codes, admit date(s), discharge date(s), ICD-10 codes and subset, payer information, payment schedules, and rebill information. Upon analytics performed utilizing the inpatient data, systematic identification of potential failures is indicated such that proposed MS-DRG's and potential reimbursement changes are communicated to relevant parties. Also, the CC/MCC capture rate (overall, surgical, and medical) is calculated for comparison to CMS established metrics, which include (but is not to be limited thereto) non-Medicaid payers for additional revenue opportunities.

In particular, the nCREAS tool is configured and operational to analysis records preferably in three-time states: 1) Initial evaluation probe; 2) Retrospective periodic; and 3) concurrent. In accordance with the illustrated embodiments, the nCREAS tool compares inpatient information provided by a client against established criteria to produce a preliminary list of inpatient records that were potentially coded and reimbursed incorrectly. Auditing consultant(s) then preferably validate the accuracy of the preliminary list against source hospital records and add supporting details. The nCREAS tool is then configured and operational to produce an easily understood and visualized report which preferably conveys return on investment if coding is corrected and the encounter is rebilled retrospectively, and over a certain prescribed time period (e.g., the upcoming year or years).

Computing device 200 is further configured and operational to provide a software tool (nCREAS Analytics) functional to analysis accounts receivables data, cash collections data, staff and account productivity data, revenue charge capture data, and denials data to preferably identify trends and high-value opportunities as well as process improvement opportunities. It is to be appreciated and understood that the aforementioned suite of tools may be utilized to identify trends and drill down to specific account data elements. Analytics compare client facilities & departments' performance by payer, RG, and denial code.

In accordance with certain illustrated embodiments, operability and functionality provided by the aforementioned software tool include: a) prescribing cash goals based on historical collection percentages and account receivable totals; b) providing investigation of takebacks; c) providing visual analytics regarding payments and goals by a Payor Group and a Plan; d) analyzing untouched inventory, which can be identified by RG; e) provide analytics regarding Accounts Receivables (ARs) in accordance with Age, Payor Group, and with analysis to effort from previous week; f) provide visual analytics regarding staff audit results and identifying training trends; g) determine and generate strategic and tactical views of denials including departmental comparison and forecasted recovery; h) determine and generate managerial and executive monthly reporting; provide root cause analysis of claim denials based upon 835 and 837 data; and generate a C-Suite level dashboard providing key performance indicators configured to enable strategic management of a revenue cycle.

In accordance with the preferred embodiments, it is to be understood that Electronic Data Interchange (EDI) is to be understood to encompass data formats used for many types of data exchange in different industries, including the medical industry to transfer data using data transfer protocols such as (but not limited to) FTP, HTTPS, IMAP, and others. A purpose of EDI is to transmit information to other companies electronically instead of using paper. With specific regards to EDI 837, it is specifically used for filing claims and for sending medical and healthcare data records to brokerage houses. Although a variety of business formats are used to transmit data, the HIPAA form 837 is one of the most common forms in healthcare. Under the EDI 837 standard, the PPI format includes the following information: 1) Description of the patient; 2) Condition for which the patient was treated; 3) Nature of service provided; and 4) Total cost of the treatment. In particular, the EDI 837 data format is typically segmented based on the nature of patient data, and generally divides the 837 transaction set into three groups: 1) 837P—This data is used for professional services offered to patients; 2) 837I—This data is for healthcare institutions, units, and medical centers; and 3) 837D—This data involves dental practices. Apart from healthcare units and medical centers, no other business unit can use EDI 837 data format even if it is linked to the healthcare industry. EDI data is sent by the providers to payers such as insurance companies, health maintenance organizations (HMOs), or government agencies such as Medicare, Medicaid, etc. And with regard to EDI 835 data it is generally known as the The Electronic Remittance Advice (ERA) which is the electronic transaction that provides claim payment information. These files are generally used by practices, facilities, and billing companies to auto-post claim payments into their systems. For instance, 835 files may be received through a clearinghouse, direct connection, or download from an EPS/Optum Pay application.

In accordance with an illustrative use, device 200 is preferably configured and operational to generate analytics regarding how a certain institution's (e.g., a hospital) targeted coding differs from other similar institutions, as well as determine and provide analytics associated with true return on investment for other institutions. In certain embodiments, a database is created operable to collect, process and store payments received by clients each MS DRG from third party payers, and to utilize this information to produce certain deliverables, as discussed herein. Additionally, data request instructions provided to clients may be revised as needed to easily facilitate uploads of this information to device/system 200. A Length of Stay (LOS) may be determined for each patient account based on the Admit Date and Discharge Date provided by a client hospital.

Additionally, CC/MCC capture rate analytics may be performed that is preferably segmented by medical and surgical DRG codes so as to compare facility data to CMS established benchmarks. For instance, if the CC/MCC capture rates differ more than 5% from CMS benchmarks, this can cause the triggering of an audit, which is advantageous for HIM organizations to understand so as to correct irregularities. It is to be appreciated this CC/MCC analysis may also encompass non-Medicare payers.

Figure 3:
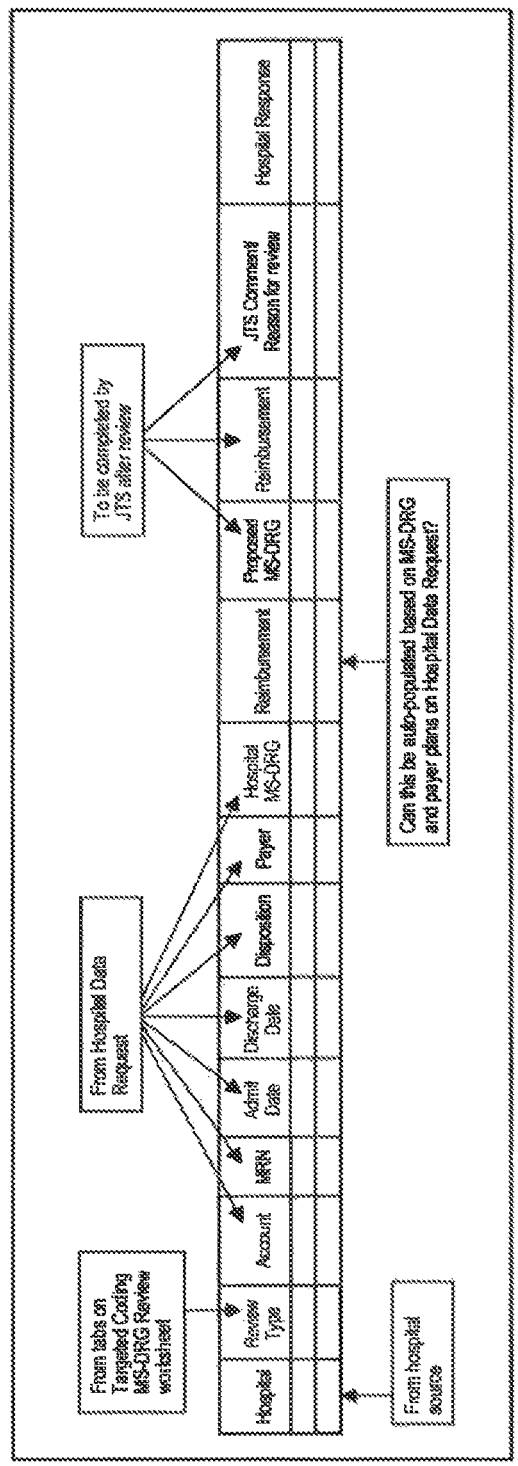
FIG. 3 depicts inpatient data compared against a Targeted Coding MS-DRG worksheet.

With reference to FIG. 3, inpatient data provided by a client may be compared against a Targeted Coding MS-DRG worksheet to determine which accounts should be reviewed, whereby a list of inpatient records to be investigated is produced. Preferably, software executing on device 200 is programmed to produce a revised or corrected list of records to be recoded based on new information and the respective return on investment.

In accordance with the preferred embodiments, device 200 is specifically configured and programmed to perform and generate four types of patient collection reports, namely: 1) Collections and Productivity; 2) Denials; 3) Accounts Receivable; and Auditing, the functionality of each is herein briefly discussed. Starting with the Collections and Productivity Report, it preferably includes a: a) Cash Report that tracks a collections goal by payer and illustrates an accurate projected cash for the month (see, FIG. 5); b) Productivity Report that illustrates contribution to cash and productivity goal based on accounts worked and hours; c) Account Inactivity Report that analyzes when staff works on certain inventory accounts, which preferably includes a top 'Days' row indicating the last time in days when a user worked on a certain account (see, FIG. 7); and d) Collection Rate that illustrates gross and adjusted collection rate by payer (see, FIG. 6).

With regard now to a Denial Collections Report, it preferably includes a: a) Overview section indicating the number of denials by month by a certain department, which may be segmented by denial code and payer (see, FIG. 10); b) Denial Status Analysis section indicating denials by a department and if they are in-progress or to be worked upon (see, FIG. 11); c) Recovery Opportunity Analysis section that illustrates recovery rate/dollars by a department preferably based on historical performance (see, FIG. 12); and d) Location Analysis section that compares different facilities denial rate by code and payer.

Figure 8:
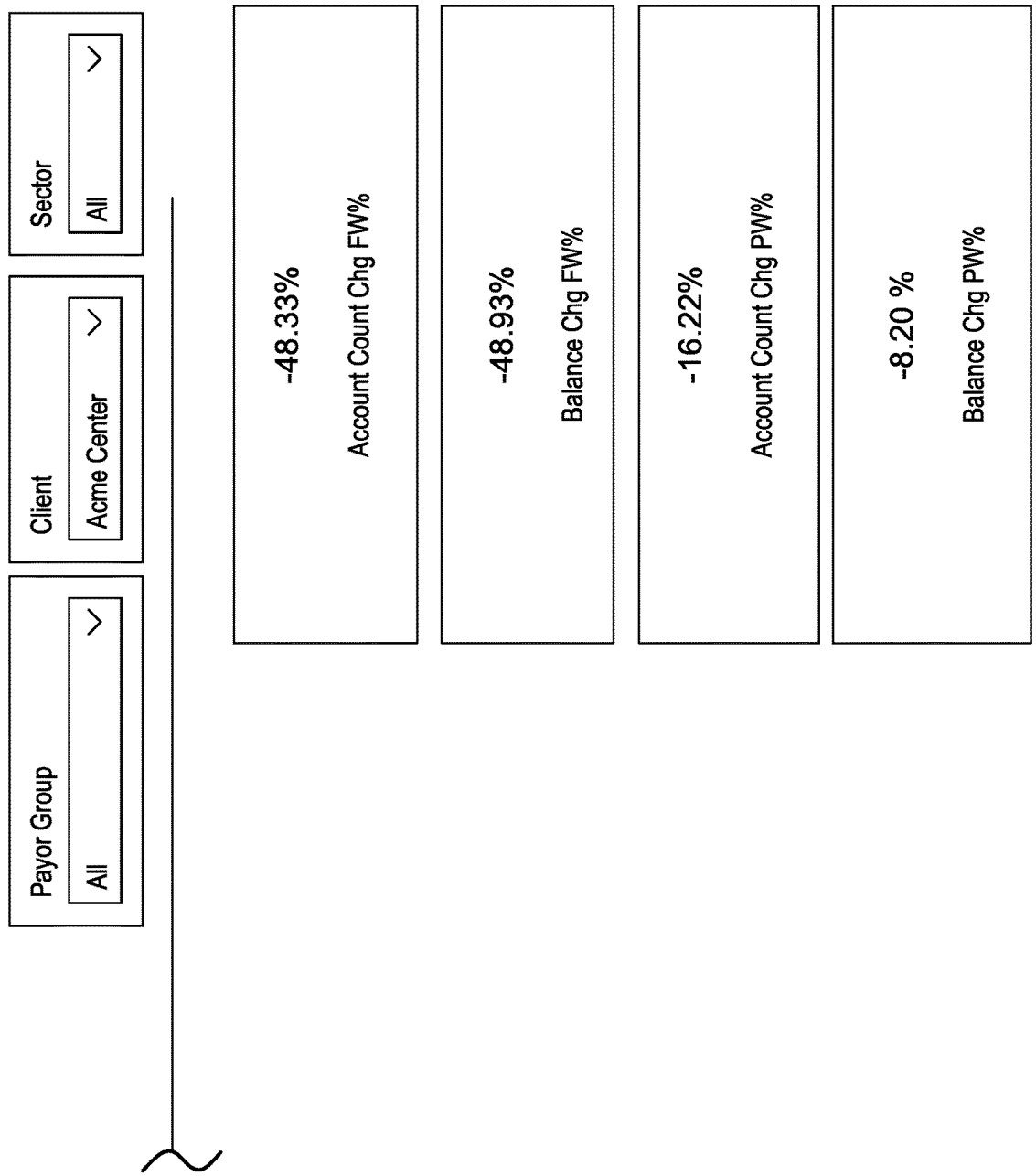
Figure 9:
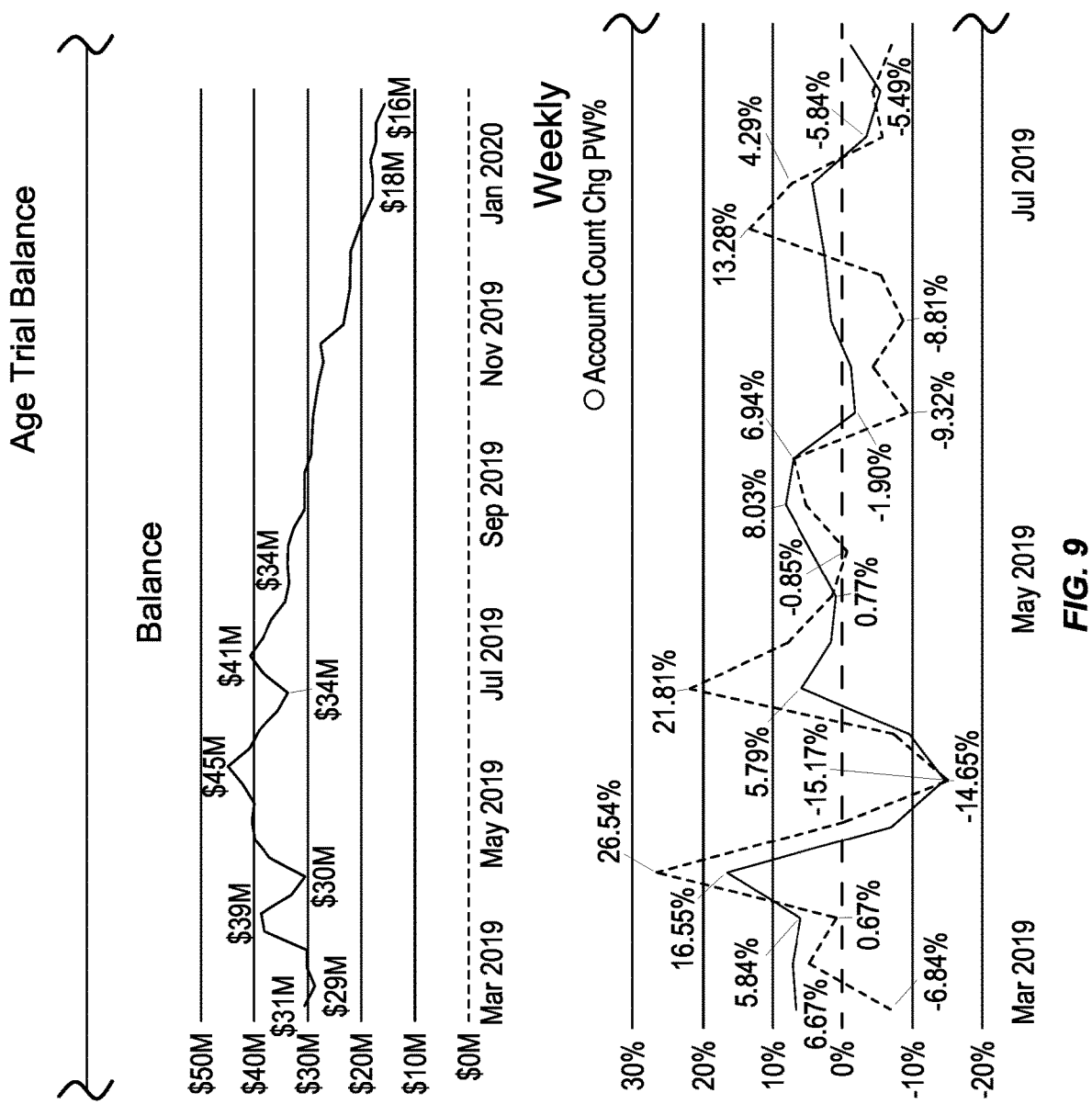
Figure 9:
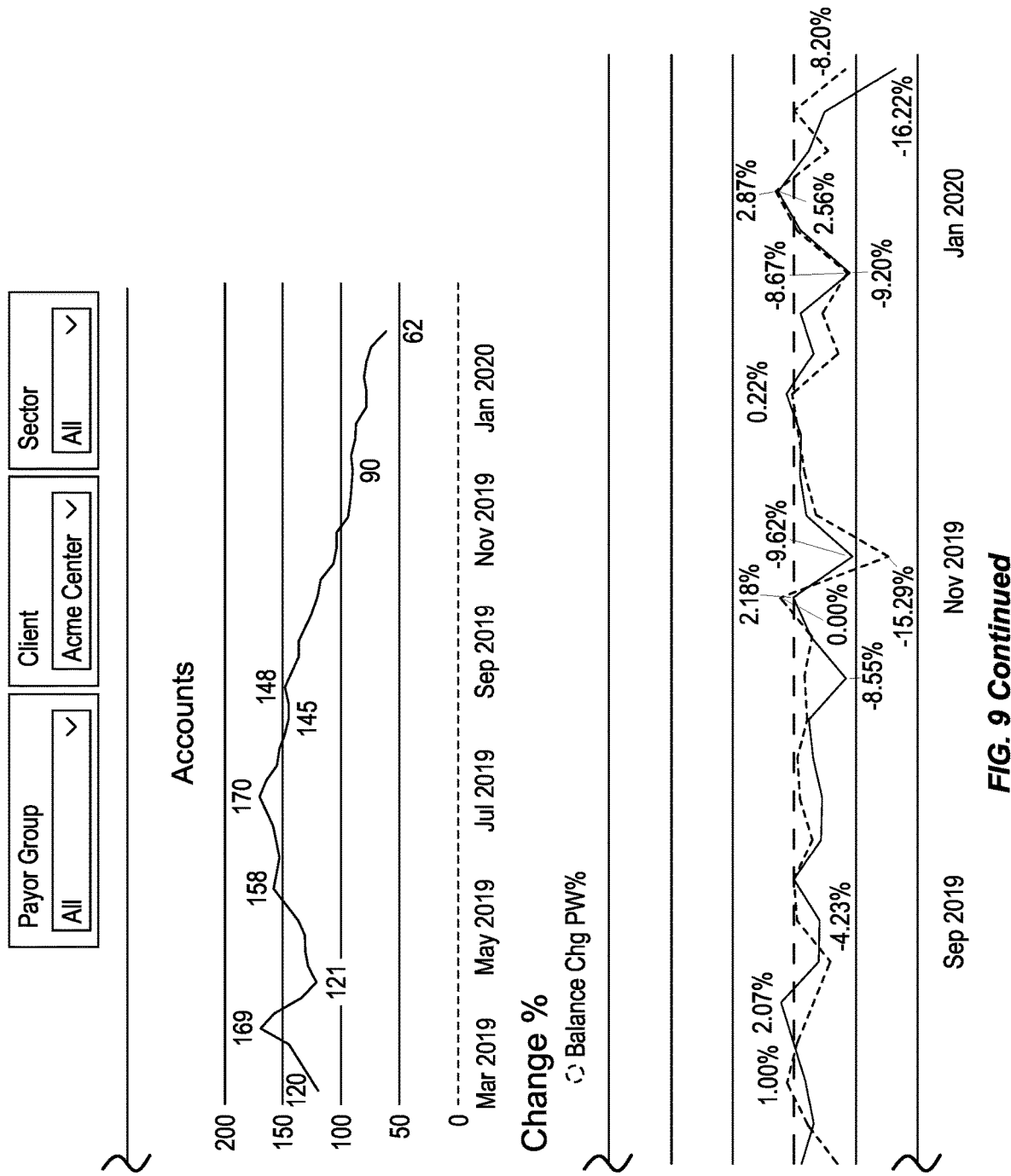

With regard to an Accounts Receivable Collection Report, it preferably includes a: a) New Accounts in Inventory section illustrating new accounts and dollars preferably by week/month/year; b) Age Trial Balance section that segments accounts by Payer, Plan, IP/OP, Age and account number (see, FIG. 8); and c) Age Trial Balance section that preferably consists of a graph caused to be generated on a user's GUI that illustrates trends by accounts and balances preferably over a certain prescribed time period (e.g., a week) in a department's AR (see, FIG. 9).

And with regard to an Auditing Collection Report, it preferably includes a: a) Auditing Results section that illustrates each auditing category and score by staff member preferably over a selected period of time; b) Detail section that provides account level detail and auditors notes providing a simplified method to review an audit score for each staff member; c) Executive Summary section that illustrates a high level summary on how each team is performing; and d) Training section that preferably illustrates trends by auditing category providing simplified recognition of when to engage in a re-training session.

Figure 4:
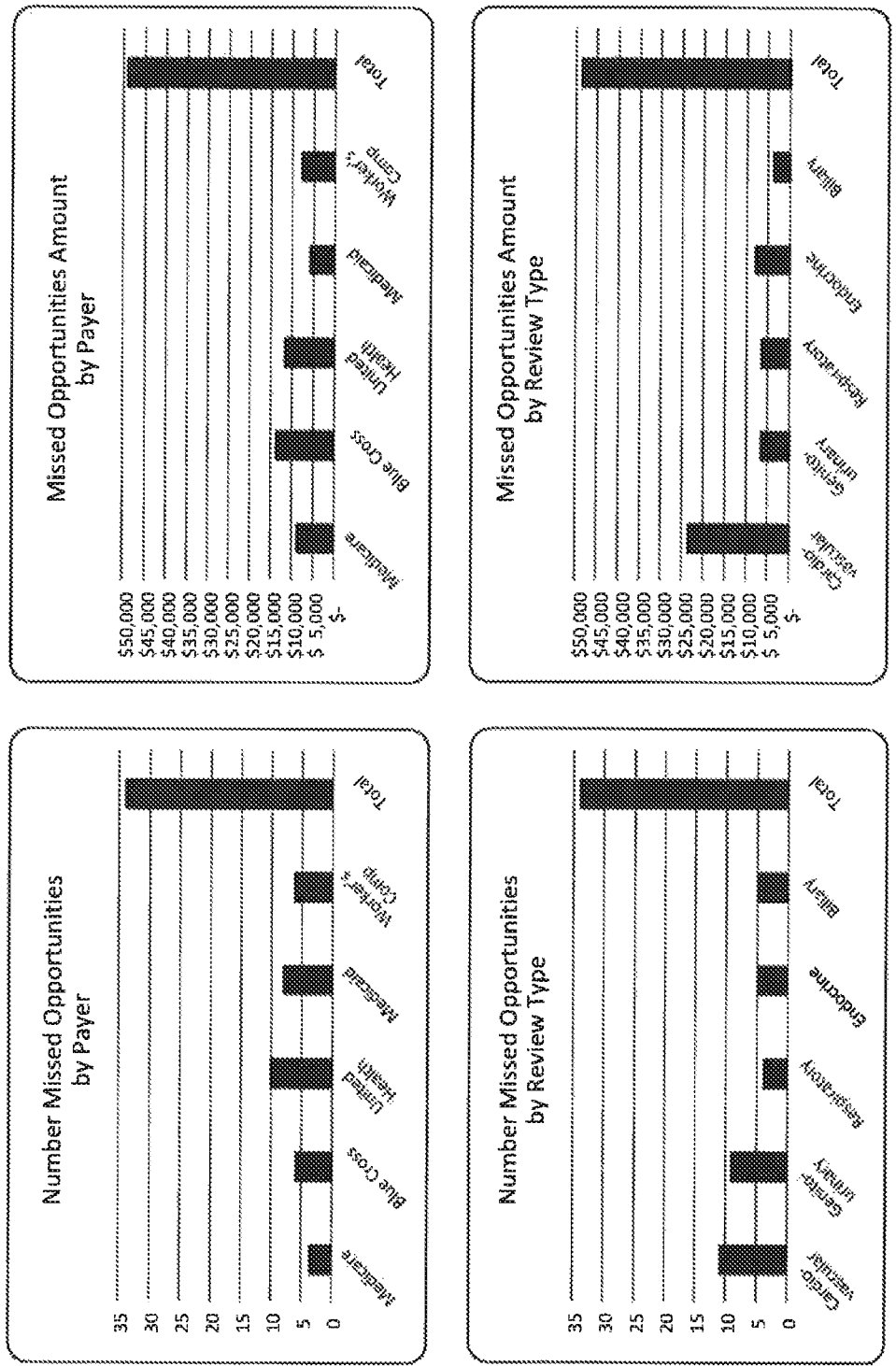
FIG. 4 depicts a graphical report accepting parameters of a specified time period for generating a list of records that can be recoded and/or rebilled.

With reference now to FIG. 4, a graphical report is provided that accepts parameters of a specified time period and client to be entered so as to produce an electronic list of the records that can be recoded, rebilled or both. This report is preferably based on an action plan developed with a client.

With regards to specific exemplary reports capable of being generated by device 200 upon performance of data analytics discussed herein (which reports are preferably generated via a GUI on a user's computer display device (e.g., 224)), and starting with FIG. 5, shown is a Cash Report 500 for a user prescribed time period 502 (e.g., Dec. 1, 2019 to Dec. 31, 2019) wherein the user selected Payor Group 504 is "All", the user selected Client 506 is "Acme Center" and the user selected Sector 508 is "All". Exemplary Cash Report 500 is shown to include two primary sections, namely Daily Cash Collections 510 and Goal Attainment 512. It is noted the Daily Cash Collections 510 includes a Net Payments section 514 which preferably includes a hierarchy view enabling a user to drill down to summarize data by payor group, plan and receivable group bill period, and a Takeback section 516, which preferably identifies takebacks to enable investigation of the cause of the takeback. And with regard to the Goal Attainment section 512, it preferably provides a Monthly Goal section 518 that preferably indicates AR and understands what will flow into the applicable inventory and project a monthly goal based on historical collections. For instance, if an account is paid before it reaches inventory, the monthly goal will understand and adjust the goal, which goal is also adjustable by percentage of AR.

Figure 6:
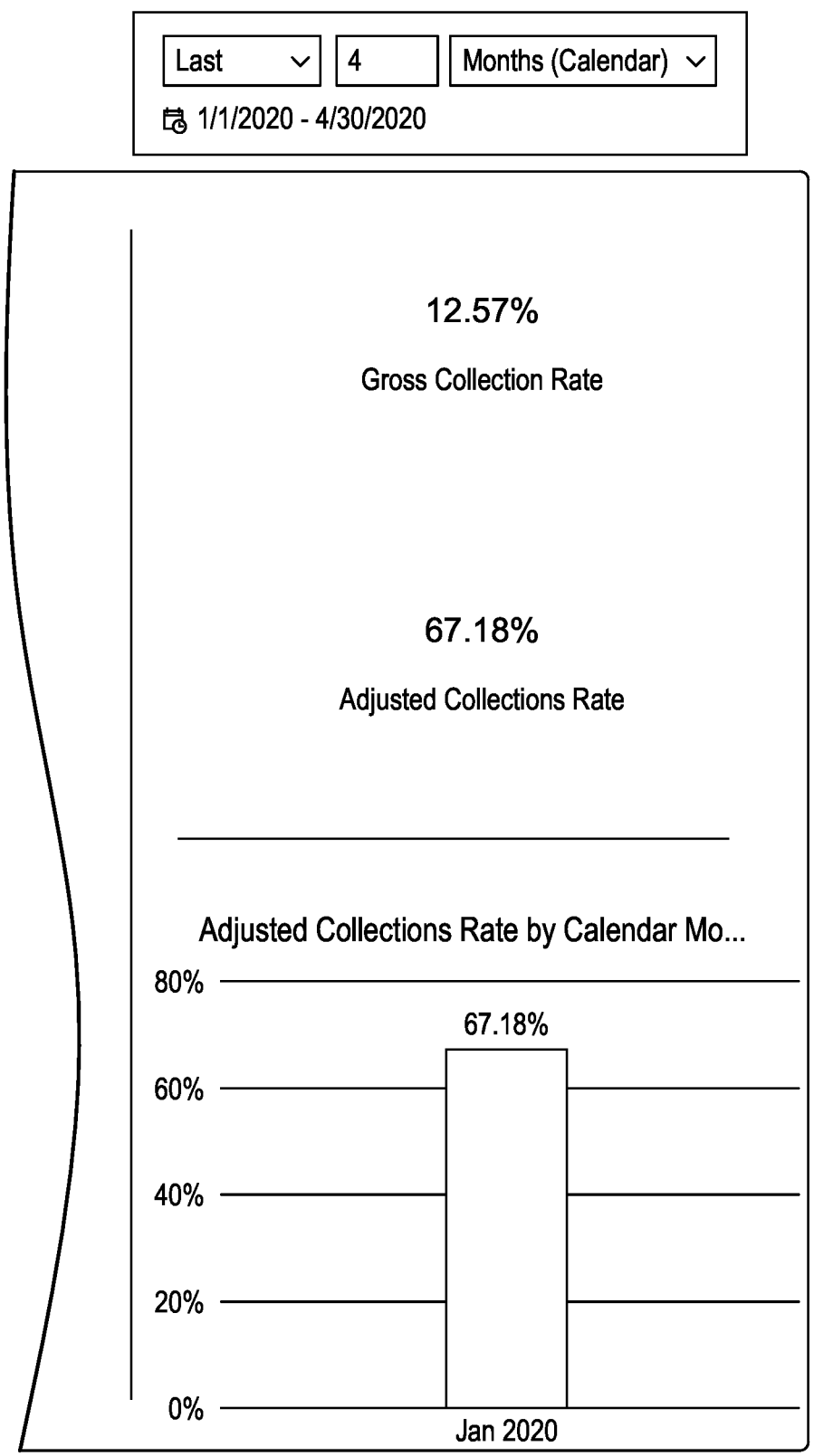

With reference to FIG. 6, shown is an exemplary Collection Rate Report 600 for a user prescribed time period 602 of Jan. 1, 2020 to Apr. 30, 2020 wherein the user selected Payor Group 604 is "All", the user selected Client 606 is again "Acme Center" and the user selected Sector 608 is "All". The exemplary Collection Rate Report 600 is shown to include two primary sections, namely Cash Collections Rate 610 and collection Rate 612.

With reference to FIG. 7, shown is an exemplary Account Inactivity Report 700 which preferably indicates analysis of when staff touches accounts in an inventory. For instance, the top 'Days' row 710 indicates the last time in days when a user touched a certain account. The goal of this reporting is to ensure no account is forgotten or unworked. This report can preferably be sorted by payor and by Receivable group, such that a user can readily identify accounts with large balances that need to be followed-up on a priority basis.

With reference to FIG. 8, shown is an exemplary Age Trail Report 800 wherein the user selected Payor Group 804 is "All", the user selected Client 806 is again "Acme Center" and the user selected Sector 808 is "All". And shown in FIG. 9 is the Age Trail Report (800) indicated in graphical format 900.

Figure 10:
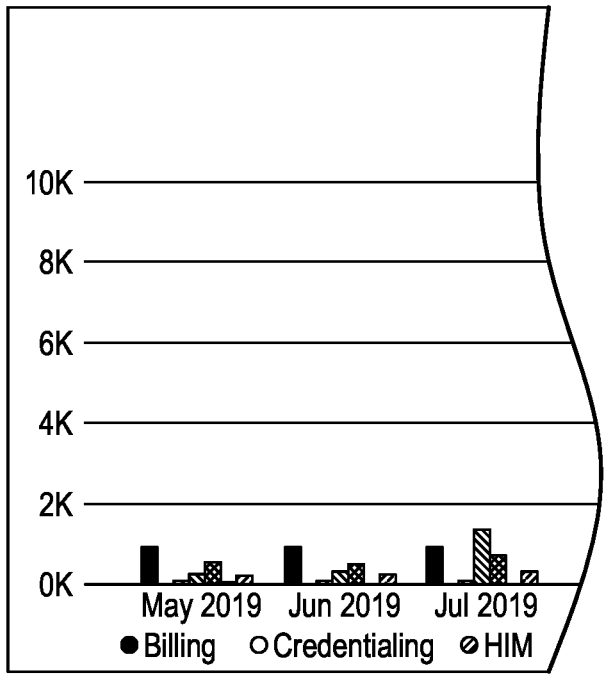
Figure 10:
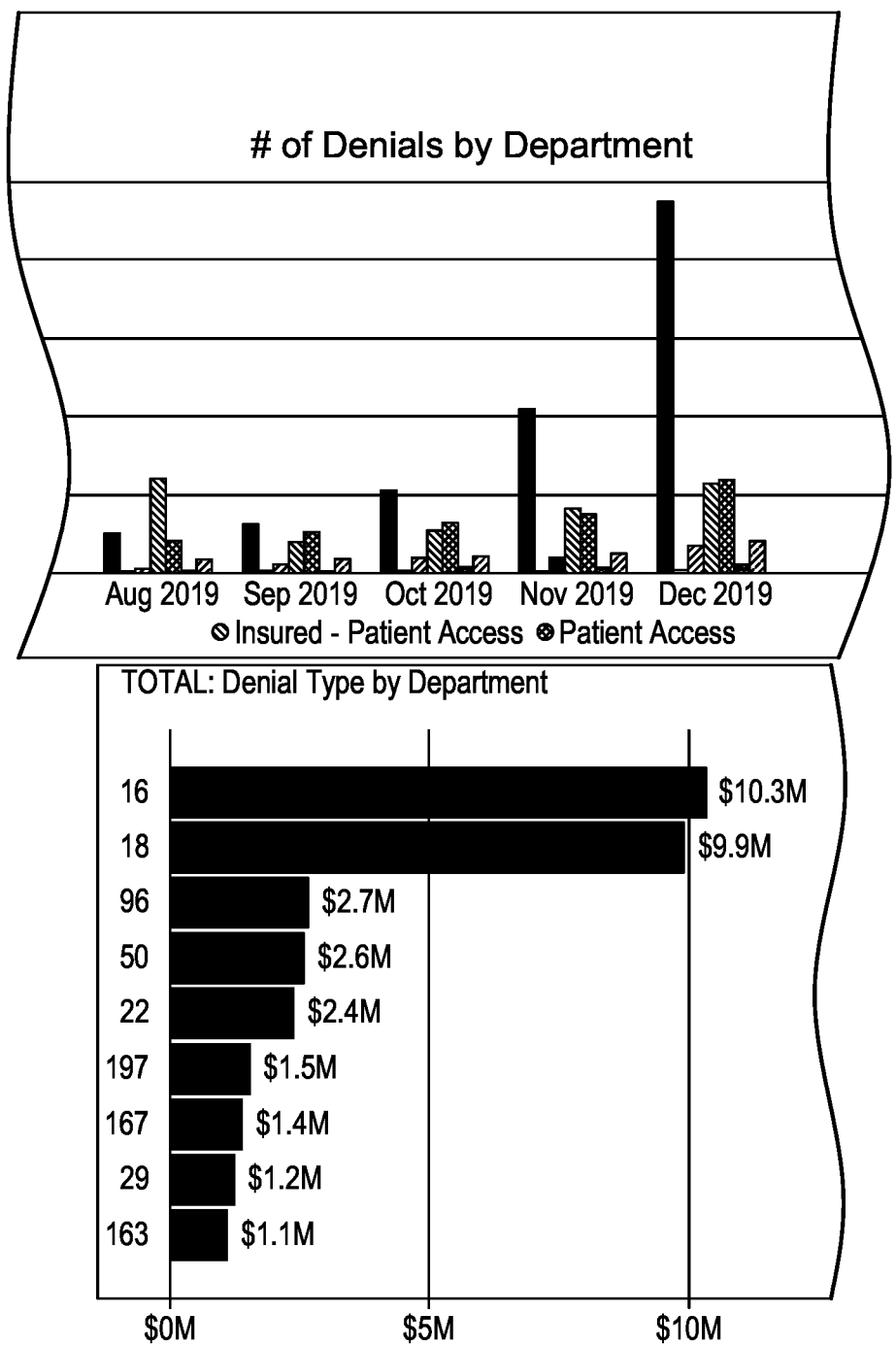
Figure 10:
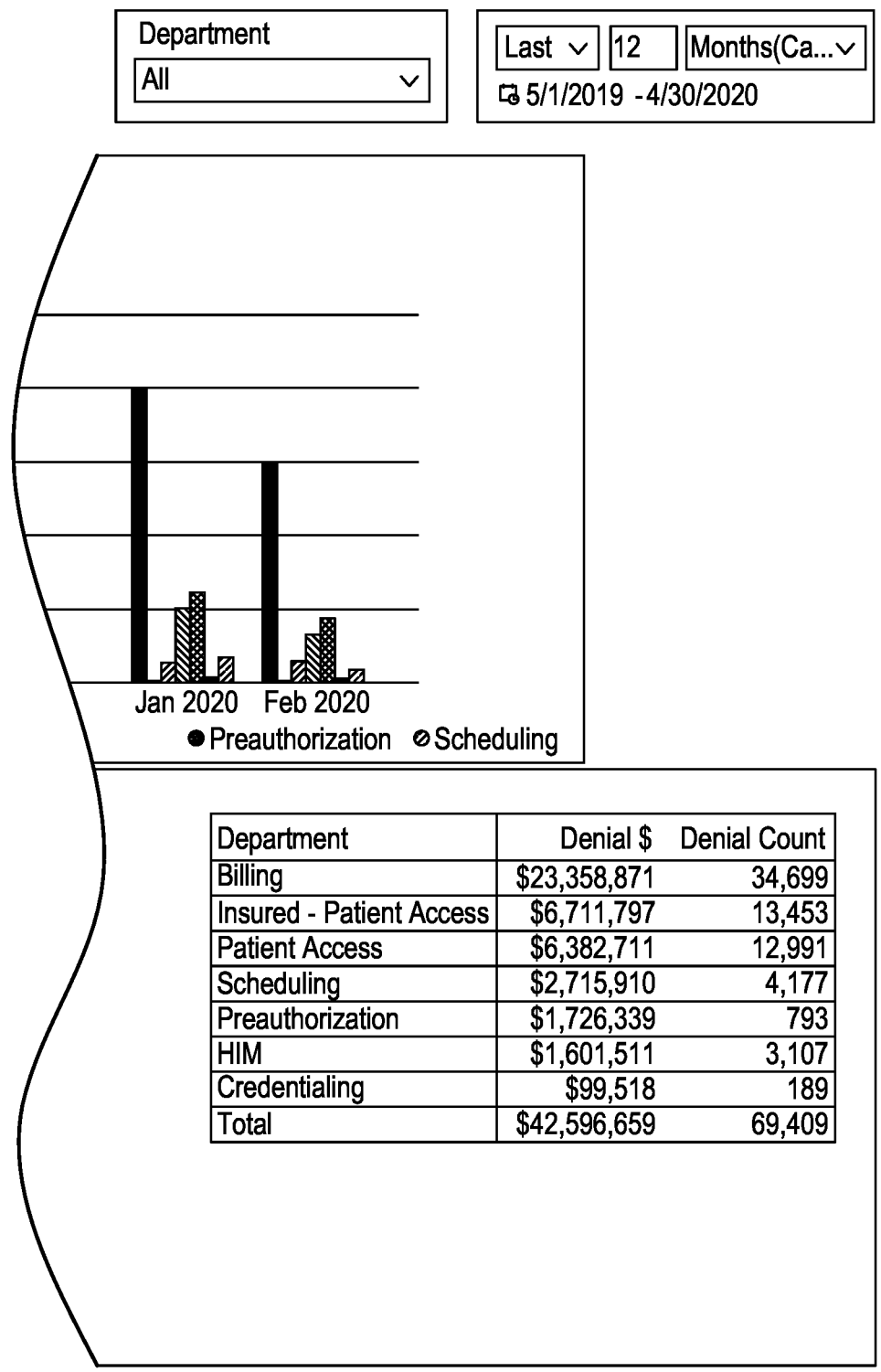
Figure 11:
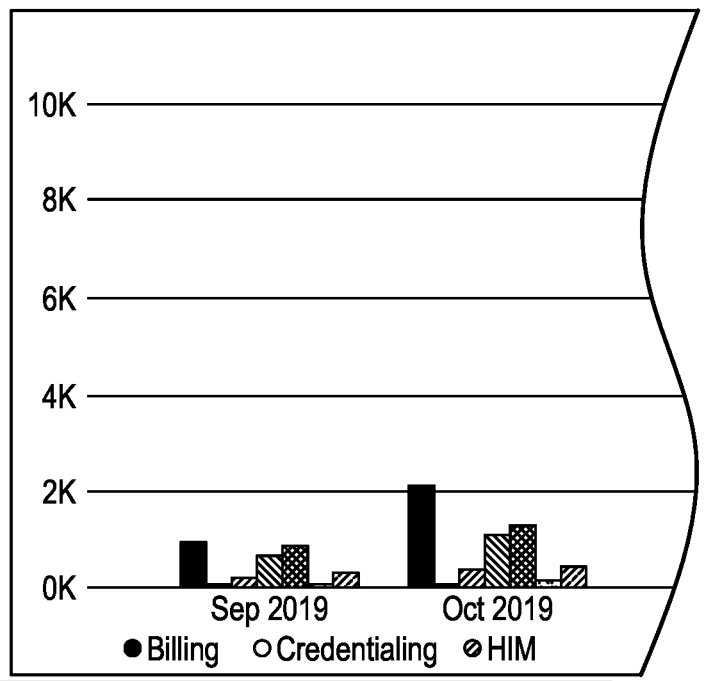
Figure 11:
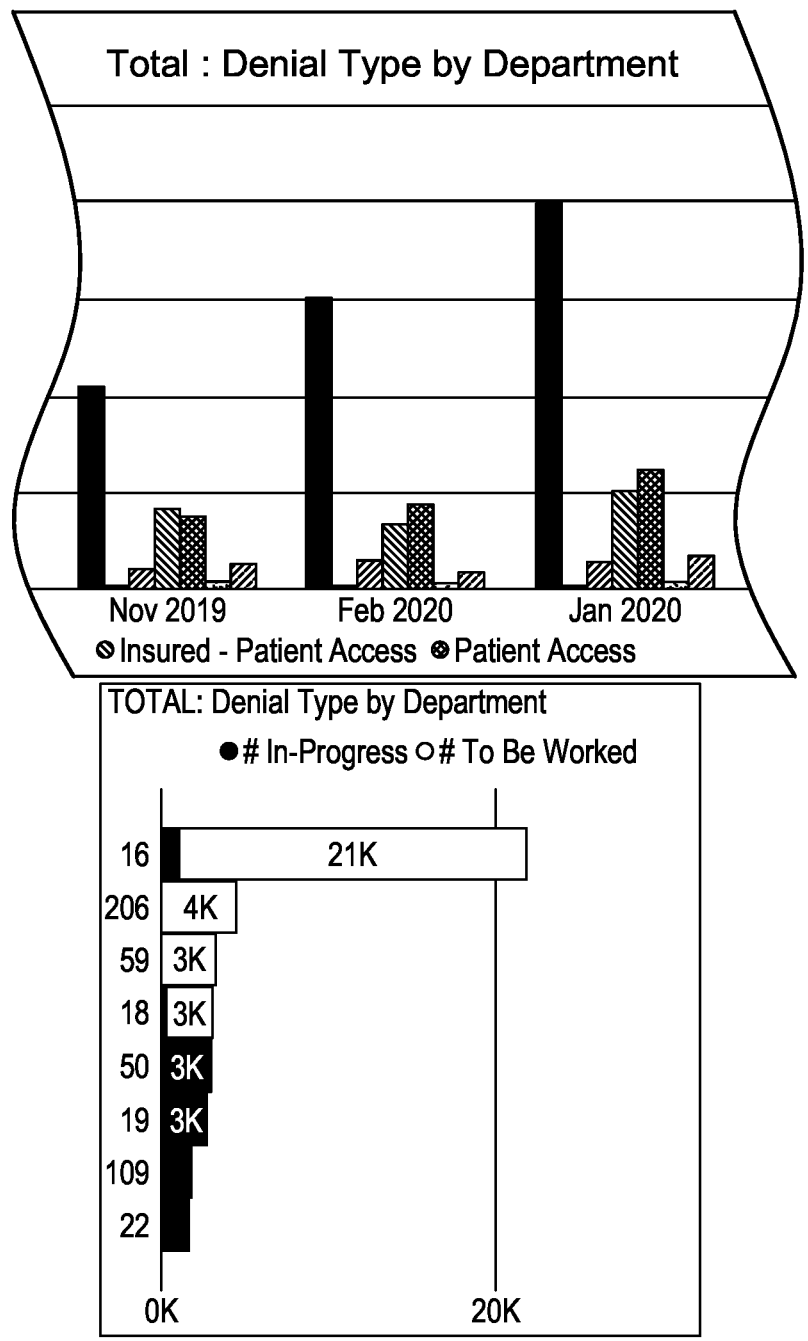
Figure 11:
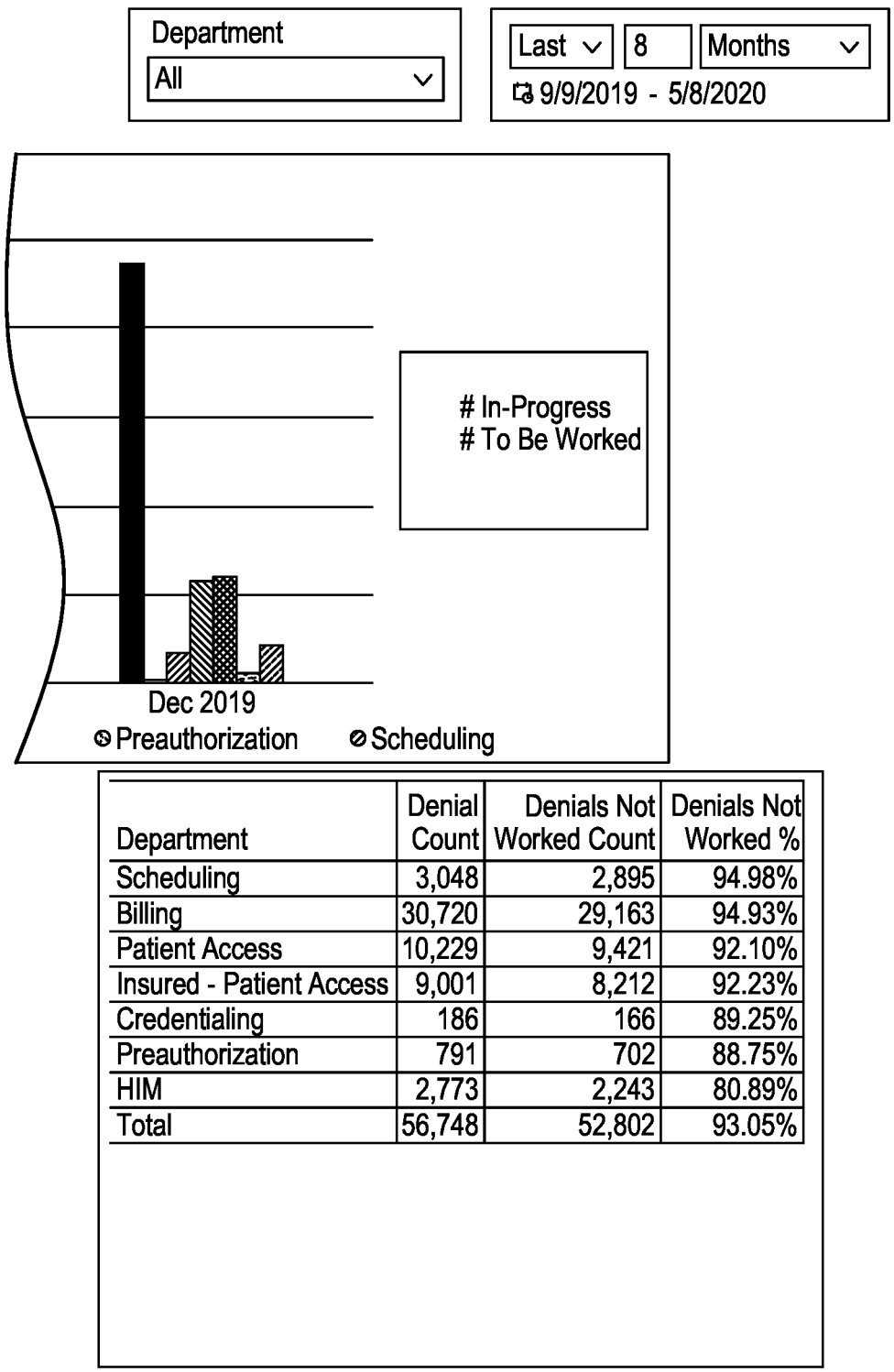
Figure 12:
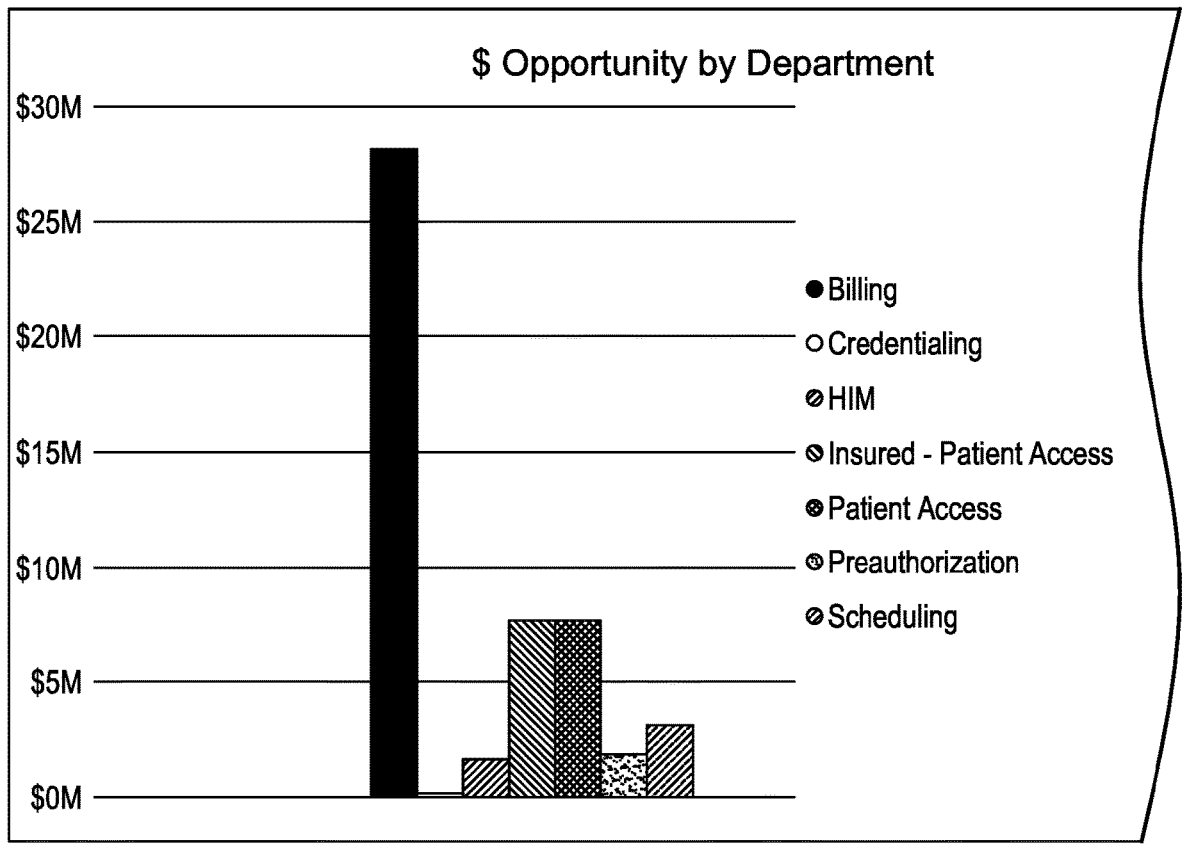
Figure 12:
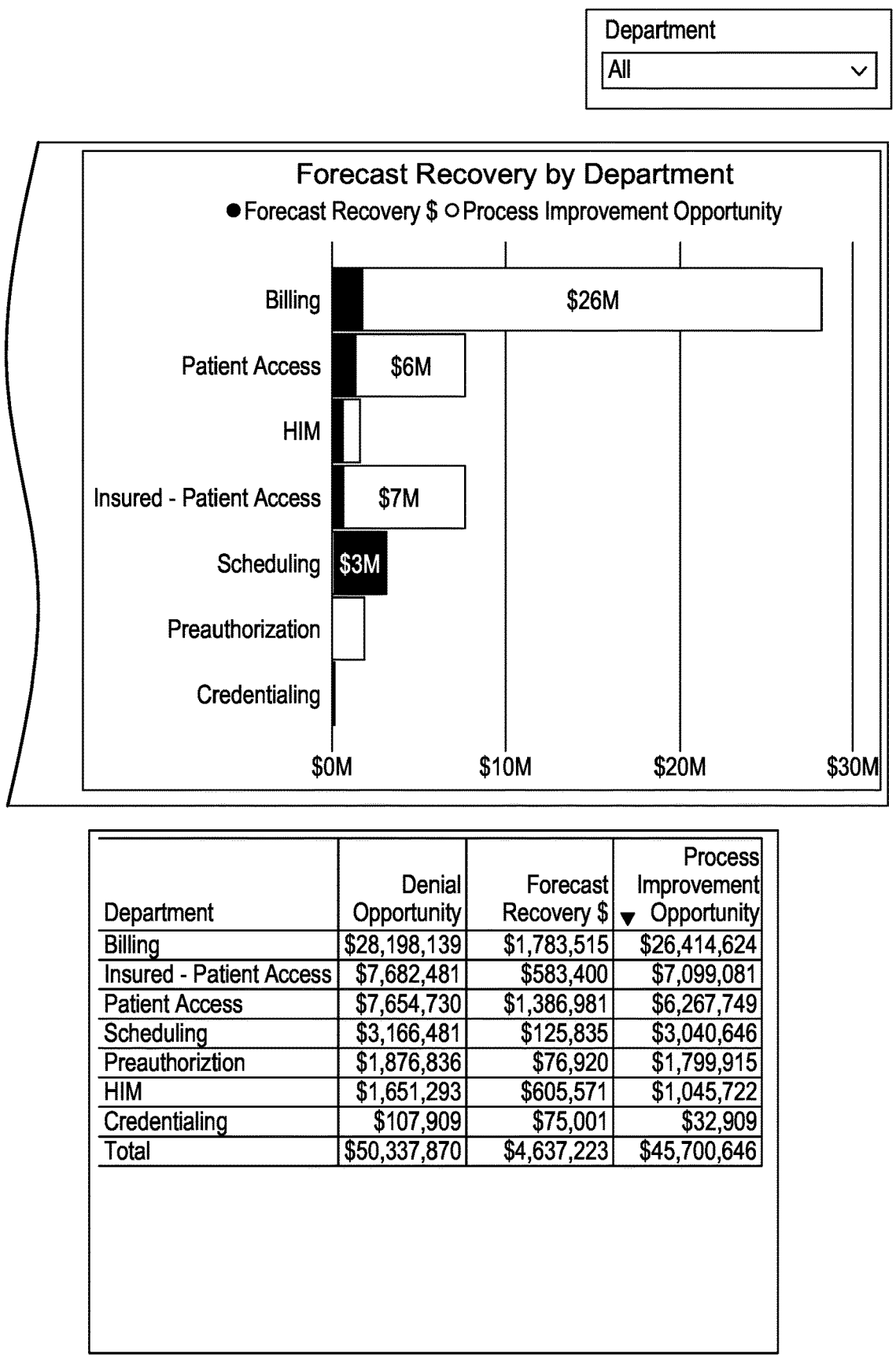

With reference to FIG. 10, shown is an exemplary Denials Management Report 1000 wherein the user selected Department 1002 is "All", and the user selected time period 1004 is May 1, 2019 to Apr. 30, 2020. FIG. 11 depicts the associated Denial Status Analysis report 1100, and FIG. 12 depicts the associated Recovery Opportunity Analysis report 1200.

It is to be understood and appreciated that functional advantages provided by the above illustrative embodiments include (and are not to be understood to be limited to) providing identification of billing related instances resulting in reduction of lost revenue caused by incomplete or inaccurate coding as well as providing retrospective correct coding and rebilling third party payors following systematic identification of billing irregularities. Also provided is an autonomous electronic method to concurrently identify and correct coding and billing errors and generating visualized reports that convey patterns, opportunities, and return on investment of retrospective or concurrent corrected coding.

In other illustrated embodiments, the nCREAS system/device 200 is further configured and operative to provide the following functionality (each is described in turn below): 1) determine a financial health rating score value; 2) determine an Accounts Receivable (A/R) score value; and 3) determine Non-Fungible Tokens (NFTs) from determined claim settlement rights so to be preferably used for collateral purposes.

I. Financial Health Rating Score Value

The nCREAS system/device 200 may be configured and operative to enable hospitals to determine a current internal state of their revenue cycle performance by preferably measuring certain average values in conjunction with correlations of various indicators of industry accepted accounts receivable performance, cash management and liquidity. This is preferably determined in real time so as to generate useful assessments along with a risk-weighted index which is configured for use in supporting loan underwriting (e.g., such as a FICO score value). In this embodiment, the nCREAS system/device 200 preferably determines A/R valuation and performance, which is preferably measured by a proprietary Score or Index (e.g., a Financial Health Rating score value).

The Financial Health Rating score value is preferably determined whereby various revenue cycle management measures are correlated on an automated basis and monitored in real time to assess current claim collections. That determined data is then utilized to calculate a risk-weighted index and/or score to indicate liquidity and cash flow benchmarks. Accordingly, based upon such calculations, accurate accounts receivable management performance and liquidity position are assessed to enable working capital underwriting on an automated basis.

For instance, and with reference to FIG. 13, the nCREAS system/device 200 determines, calculates and analyzes account receivables with regard to providing a scoring value, whereby various statistics are collected and compiled into a score or index value such that the effectiveness of one or more financial accounts may be determined at the claim procedure level. It is to be appreciated the aforesaid embodiment of nCREAS system/device 200 (FIG. 13) provides improvements over analogues known systems by providing an assessment of financial capacity including cash conversion cycle as well as revenue cycle performance metrics, in contrast to current known systems which only provide receivables performance parameters measured as only part of an overall cash management and liquidity position. Additionally, the nCREAS system/device 200 determines timeliness of measuring cash conversion cycle (e.g. liquidity) in contrast to known systems which only determined market valuation by considering an account as merely a wider sampling of liquidity parameters, which is disadvantageous as it does not provide analysis of a market in a timely fashion. Further, the nCREAS system/device 200, and as shown in FIG. 13, calculates score values preferably at a % of total points, preferably with categories of low, medium, medium high, and high score earners.

II. A/R Rating Score Value

Figure 14:
FIG. 14 illustrates a claim valuation process in accordance with an illustrated embodiment.

The nCREAS system/device 200, and with reference now to FIG. 14, may be configured and operative to enable evaluating a risk of full payment of claims and grouping claims from one or more service provider(s) based on a commonality of risk. Additionally, it preferably generates a risk-weighted score representative of the risk of the grouped claims. More specifically, it evaluates the risk of full payment which includes comparing each individual claim preferably to a database of historical performance of a service provider, and of similar claims and, moreover, evaluating for each claim an expected payment amount and an expected time (or delay) of payment by an obligor for purposes of underwriting a loan.

In use, an illustrative embodiment of the nCREAS system/device 200 preferably generates data premised upon historical collection experience of a healthcare provider's claims, whereby such data preferably includes a net collectible value matrix indicating a number of claims actually paid by individual payors (e.g., patients and medical insurance companies, and a time-to-payment histogram). The nCREAS system/device 200 further preferably tracks pools of claims using statistical data which preferably includes a net collectible value matrix that includes a number of claims paid and the standard deviation of such percentage. Additionally, it further preferably includes a collection histogram for payment timing from the billing date of the service. The nCREAS system/device 200 then assigns a risk weighted score on an automated basis, which is preferably an index/proxy on the service provider(s) indicative of the efficiency of their claims collection process.

Additionally, the nCREAS system/device 200 is further configured and operative to valuate, and preferably re-valuates individual claims, and the relative score in real-time, to update contemporaneously and continuously the bankable value (e.g., the primary advance rate, of the service provider(s) claims). It is to be appreciated and understood it is advantageous to provide a system that obviates using third-party rating agencies, and to provide a scoring system that enables lending institutions to underwrite such cash flows as collateral for financing. For instance, exemplary criteria that may be used for a claim rating component includes (and is not limited to) Payor Type, plan type, propensity to deny, contract terms, procedure code, DRG, HCSPCS, and the like, is utilized preferably in a real time rating computer process to determine payment expectancy of claims (timeliness).

III. Non-Fungible Token Determination and Generation

Figure 15:
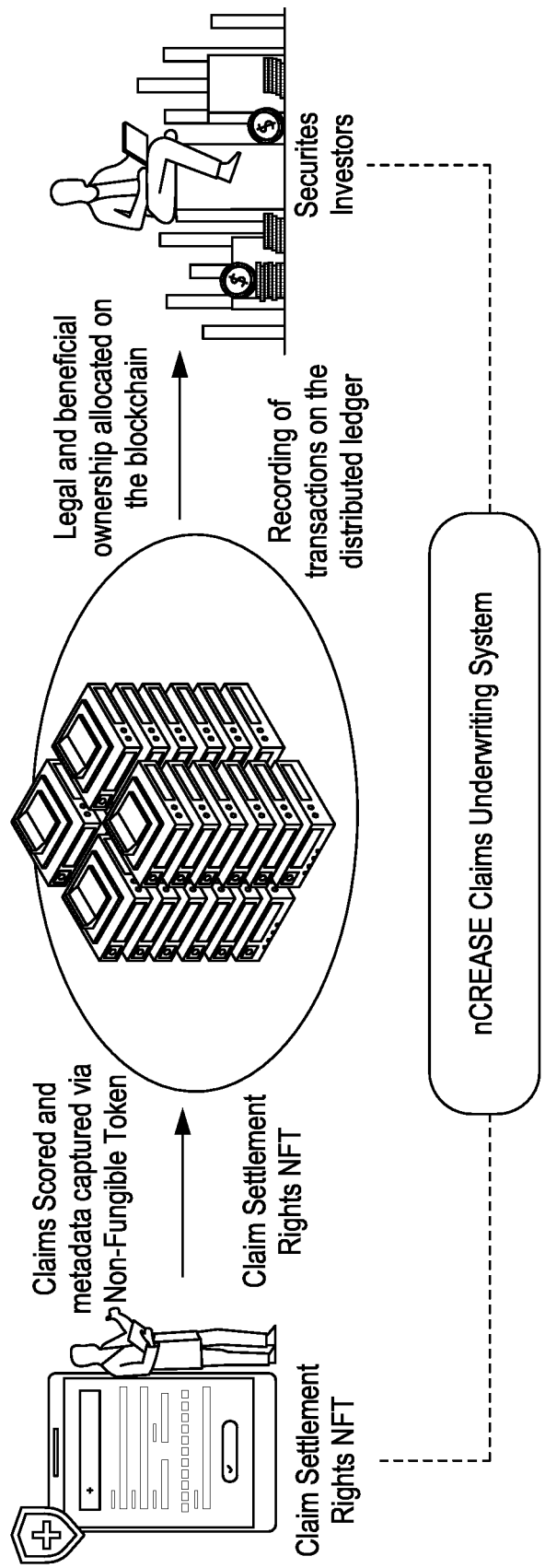
FIG. 15-17 illustrates a rights to settlement process for generating non-fungible tokens in accordance with an illustrated embodiment.
Figure 16:
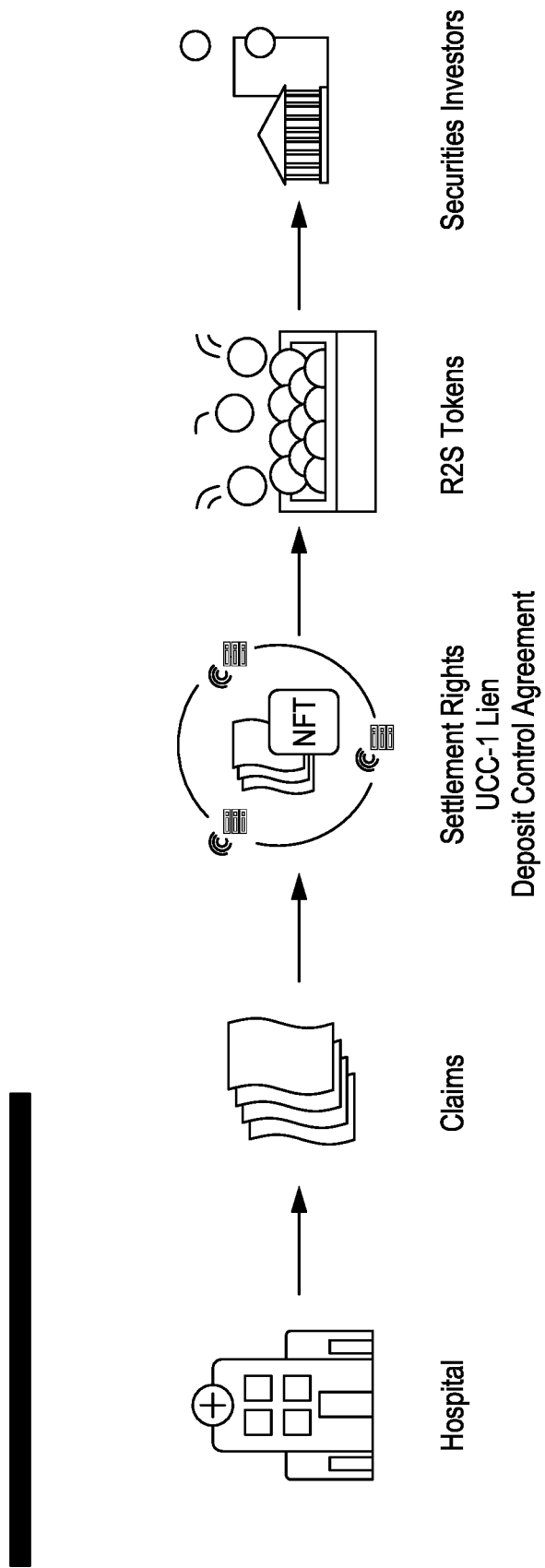
Figure 17:
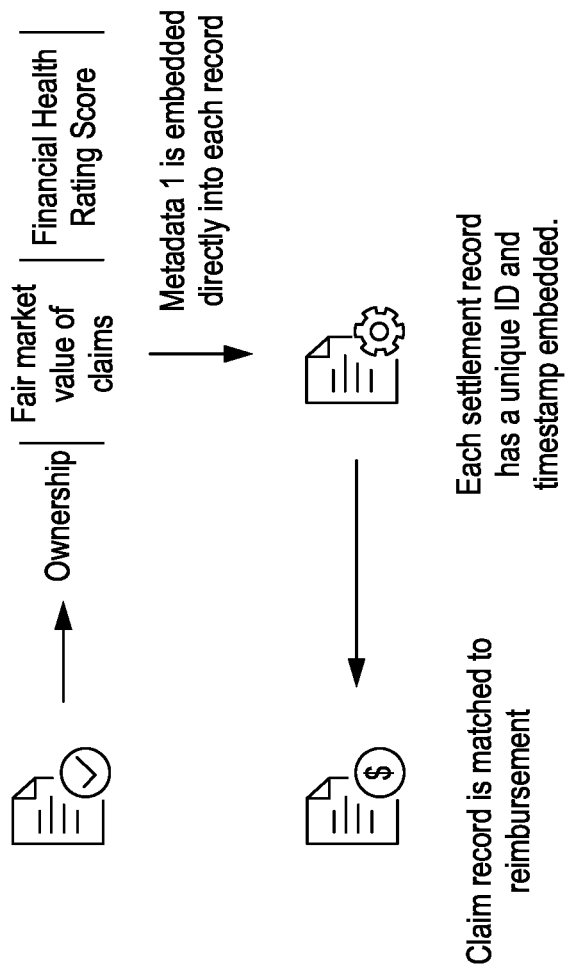

The nCREAS system/device 200, and with reference now to FIGS. 15-17, is further configured and operative to provide claim settlement rights represented as non-fungible tokens (NFT) and/or data tokens, which preferably serve as an interface for a hospital to connect claim data assets with a loan and finance underwriting system. It is to be appreciated that NFTs are blockchain-based tokens that each represent a claim settlement asset, which is an irrevocable digital certificate of ownership and authenticity for a given asset.

Preferably, the digital asset contractual details, access rights, and ownership rights are stored in a decentralized ledger database, wherein the nCREAS system/device 200 utilizes the ledger to record and/or manage property rights for the claim-based digital asset. Preferably, blockchain token ownership is transferred to a new owner after authentication and verification, which are preferably based on decentralized ledgers within a peer-to-peer network. It is to be appreciated and understood this provides real-time execution and settlement.

In accordance with the illustrative embodiment, the nCREAS system/device 200 preferably includes claim data inclusive of the aforesaid financial health rating score value (FIG. 13) and the aforesaid A/R rating score value (FIG. 14) as non-fungible tokens (NFTs), or primitives to represent and govern cash flow entitlements (e.g., settlement rights from government and insurance claim payments), preferably in escrow. The nCREAS system/device 200 is configured and operative to preferably capture obligations/settlement rights in a crypto-native, private, verifiable, and secure process preferably supporting on-chain document validation and access to claim reimbursement-related data (e.g., block chaining). The nCREAS system/device 200 is further preferably configured and operative to digitally file a UCC-1 financing statements on the NFT, preferably under the collateral category "investment property," (e.g., encompasses securities and other security-like financial assets). The nCREAS system/device 200 is further preferably operative and configured to manage terms of use of the NFT, preferably including transfer of ownership. Thus, the nCREAS system/device 200 generates an immutable record, including ID, hashes, and a status on a blockchain, as a single authoritative copy of a transferable NFT record, as well as providing for secure wallet creation and NFT storage.

Figure 18:
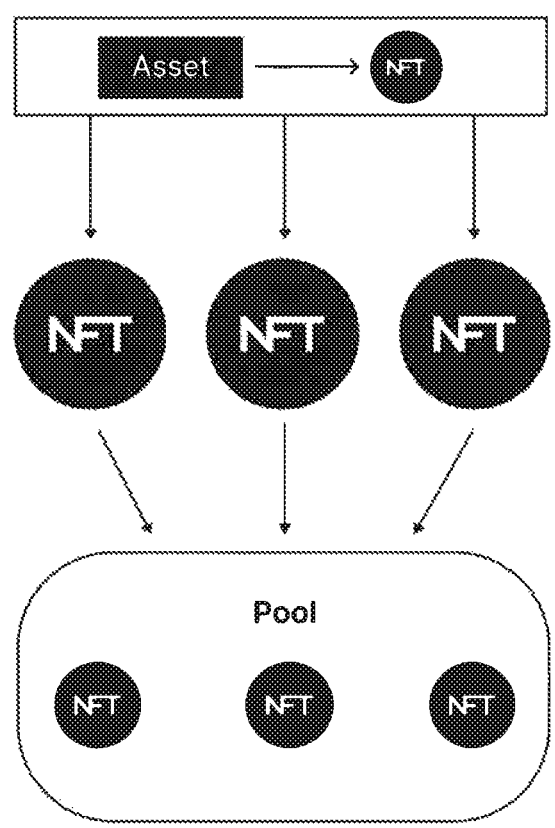
FIG. 18 illustrates a system level diagram for pooling multiple NFT assets.

With reference now to FIG. 18, it is to be further appreciated that the nCREAS system/device 200 is configured to pool multiple NFT assets together so as to allow lenders to provide financing for the pooled multiple NFT assets, in contrast to each asset individually. Thus, after an asset is tokenized and an NFT is minted on-chain, the NFT is used as a representation of the off-chain collateral for an asset linked to a loan pool, as shown in FIG. 18. Preferably, the asset is priced via the nCREAS system/device 200 for enabling an issuer or company to borrow liquidity from the pool, such that, preferably the accruing debt per NFT asset is repaid by the issuer or company, including interest payments and principal repayments over a certain time period. Thus, the nCREAS system/device 200 creates on-chain, asset level transparency whereby a lender can view which assets (e.g., NFTs) a pool contains, what has been borrowed against and repaid, what is overdue, and the like. This is particularly advantageous as it creates an immutable, transparent track record of financial transactions that can be publicly verified and audited The nCREAS system/device 200 is further preferably configured and operative to digitally govern tripartite agreements, preferably via a smart contract between hospitals and lenders (known as "account control" or "deposit control agreements") whereby the hospital grants the security interest in the NFT, with the NFT being preferably held in a specific account (or wallet) with a third-party custodian. That third party, in turn, preferably agrees to adhere to the directions of the lender, thereby giving the lender "control" of the NFT and thus perfecting their interest for use as collateral.

With certain illustrated embodiments described above, it is to be appreciated that various non-limiting embodiments described herein may be used separately, combined or selectively combined for specific applications. Further, some of the various features of the above non-limiting embodiments may be used without the corresponding use of other described features. The foregoing description should therefore be considered as merely illustrative of the principles, teachings and exemplary embodiments of this invention, and not in limitation thereof.

It is to be understood that the above-described arrangements are only illustrative of the application of the principles of the illustrated embodiments. Numerous modifications and alternative arrangements may be devised by those skilled in the art without departing from the scope of the illustrated embodiments, and the appended claims are intended to cover such modifications and arrangements.

What is claimed is:

1. A non-transitory computer readable medium comprising computer executable instructions configured to cause a computer to perform a method for generating non-fungible tokens (NFTs) representing a company asset based on evaluation of company assets, wherein the company is a hospital and the assets owed to the company include settlement rights, the method comprising:
   storing in a database one or more digital assets representative of contractual obligations owed to the company, wherein the one or more digital assets include one or more of settlement rights and insurance claim payment obligations;
   analyzing the one or more digital assets in the database to determine one or more assets owed to the company;
   determining a valuation value for the determined one or more assets;
   generating a NFT based on the determined valuation value of the determined one or more assets, wherein generating the NFT comprises generating an immutable record including ID, hashes and a status on a blockchain as a single authoritative copy of a transferable NFT record; and
   digitally filing a UCC-1 financing statement utilizing the generated NFT, thereby leveraging the generated NFT as collateral in an underwriting process.

2. The computer method as recited in claim 1, further including analyzing, in real-time, a revenue cycle management of the company to generate a risk-weighted index value indicative of the revenue cycle management.

3. The computer method as recited in claim 2, further including utilizing the generated risk-weighted index value for determining an A/R and performance value.

4. The computer method as recited in claim 3, wherein historical revenue cycle management performance is measured to evaluate one or more claim collection efforts for providing an assessment of accounts receivable management performance.

5. The computer method as recited in claim 2, further including determining a value of risk of full payment for grouped claims from one or more company service providers based upon a commonality of risk.

6. The computer method as recited in claim 5, further including generating a risk weighted score value representative of the determined value of risk for the grouped claims.

7. The computer method as recited in claim 5, wherein determining a value of risk of full payment includes comparing individual claim line items to a database of historical performance associated with at least one company service provider.

8. A computer system for generating non-fungible tokens (NFTs) representing a company asset based on evaluation of company assets, wherein the company is a hospital and the assets owed to the company include settlement rights, the computer system comprising:
   a memory configured to store instructions;
   a processor disposed in communication with the memory and a database, wherein said processor upon execution of the instructions is configured to:
   store in the database one or more digital assets representative of contractual obligations owed to the company, wherein the one or more digital assets include one or more of settlement rights and insurance claim payment obligations;

analyze the one or more digital assets in the database to determine one or more assets owed to the company;

determine a valuation value for the determined one or more assets;

generate a NFT based on the determined valuation value of the determined one or more assets, wherein generating the NFT comprises generating an immutable record including ID, hashes and a status on a blockchain as a single authoritative copy of a transferable NFT record; and digitally file a UCC-1 financing statement utilizing the generated NFT, thereby leveraging the generated NFT as collateral in an underwriting process.

9. The computer system as recited in claim 8, wherein the processor is further configured to analyze, in real-time, a revenue cycle management of the company to generate a risk-weighted index value indicative of the revenue cycle management.

10. The computer system as recited in claim 9, wherein the processor is further configured to utilize the generated risk-weighted index value for determining an A/R and performance value.

11. The computer system as recited in claim 10, wherein historical revenue cycle management performance is measured to evaluate one or more claim collection efforts for providing an assessment of accounts receivable management performance.

12. The computer system as recited in claim 9, further including determining a value of risk of full payment for grouped claims from one or more company service providers based upon a commonality of risk.

* * * * *